(12) United States Patent
Dewey et al.

(10) Patent No.: US 7,879,104 B2
(45) Date of Patent: Feb. 1, 2011

(54) SPINAL IMPLANT SYSTEM

(75) Inventors: Jonathan M. Dewey, Memphis, TN (US); Lauren Lyons, Memphis, TN (US); Christopher M. Patterson, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 749 days.

(21) Appl. No.: 11/560,169

(22) Filed: Nov. 15, 2006

(65) Prior Publication Data

US 2008/0114456 A1    May 15, 2008

(51) Int. Cl.
*A61F 2/44* (2006.01)
(52) U.S. Cl. .................. 623/17.16; 623/17.11; 606/246
(58) Field of Classification Search .................. 606/60, 606/61, 90, 246–253, 279; 623/17.11–17.16
See application file for complete search history.

(56) References Cited

U.S. PATENT DOCUMENTS

| | | |
|---|---|---|
| 0,624,969 A | 5/1899 | Peterson |
| 1,153,797 A | 9/1915 | Kegreisz |
| 1,616,347 A | 11/1924 | Pataky |
| 1,870,942 A | 8/1932 | Beatty |
| 2,077,804 A | 4/1937 | Morrison |
| 2,299,308 A | 10/1942 | Creighton |
| 2,485,531 A | 10/1949 | Dzus et al. |
| 2,607,370 A | 8/1952 | Anderson |
| 2,677,369 A | 5/1954 | Knowles |
| 2,686,877 A | 8/1954 | Dobelle |
| 3,065,659 A | 11/1962 | Eriksson et at |
| 3,108,595 A | 10/1963 | Overment |
| 3,426,364 A | 2/1969 | Lumb |
| 3,648,691 A | 3/1972 | Lumb et al. |
| 3,779,239 A | 12/1973 | Fischer et al. |

(Continued)

FOREIGN PATENT DOCUMENTS

DE    2821678 A1    11/1979

(Continued)

OTHER PUBLICATIONS

"Dispositivo Intervertebrale Ammortizzante DIAM," date unknown, p. 1.

(Continued)

*Primary Examiner*—Eduardo C Robert
*Assistant Examiner*—Christina Negrelli
(74) *Attorney, Agent, or Firm*—Coats and Bennett, P.L.L.C.

(57) ABSTRACT

An interspinous spacer system includes a core configured to fit between adjacent spinous processes, a first fork movable relative to the core from a non-use position to an in-use position, and second fork. When in the in-use position, the first fork extends outwardly from a first side of the core and bounds an opening. The second fork extends outwardly from a second side of the core, opposite the first side, and bounds the opening. Third and fourth forks extend outwardly from the first and second sides of the core respectively and form a second opening. The second, third, and fourth forks are affixed relative to the core and relative to each other. The first fork is inserted between spinous processes in the non-use position to avoid damage to a superspinous ligament adjacent the spinous processes. Other aspects and related methods are also disclosed.

20 Claims, 18 Drawing Sheets

U.S. PATENT DOCUMENTS

| | | | |
|---|---|---|---|
| 4,011,602 | A | 3/1977 | Rybicki et al. |
| 4,237,875 | A | 12/1980 | Termanini |
| 4,257,409 | A | 3/1981 | Bacal et al. |
| 4,274,324 | A | 6/1981 | Giannuzzi |
| 4,289,123 | A | 9/1981 | Dunn |
| 4,401,112 | A | 8/1983 | Rezaian |
| 4,519,100 | A | 5/1985 | Wills et al. |
| 4,553,273 | A | 11/1985 | Wu |
| 4,554,914 | A | 11/1985 | Kapp et al. |
| 4,573,454 | A | 3/1986 | Hoffman |
| 4,592,341 | A | 6/1986 | Omagari et al. |
| 4,599,086 | A | 7/1986 | Doty |
| 4,604,995 | A | 8/1986 | Stephens et al. |
| 4,611,582 | A | 9/1986 | Duff |
| 4,632,101 | A | 12/1986 | Freedland |
| 4,636,217 | A | 1/1987 | Ogilvie et al. |
| 4,646,998 | A | 3/1987 | Pate |
| 4,657,550 | A | 4/1987 | Daher |
| 4,662,808 | A | 5/1987 | Camilleri |
| 4,686,970 | A | 8/1987 | Dove et al. |
| 4,704,057 | A | 11/1987 | McSherry |
| 4,759,769 | A | 7/1988 | Hedman et al. |
| 4,787,378 | A | 11/1988 | Sodhi |
| 4,822,226 | A | 4/1989 | Kennedy |
| 4,827,918 | A | 5/1989 | Olerud |
| 4,834,600 | A | 5/1989 | Lemke |
| 4,863,476 | A | 9/1989 | Shepperd |
| 4,886,405 | A | 12/1989 | Blomberg |
| 4,892,545 | A | 1/1990 | Day et al. |
| 4,913,144 | A | 4/1990 | Del Medico |
| 4,931,055 | A | 6/1990 | Bumpus et al. |
| 4,932,975 | A | 6/1990 | Main et al. |
| 4,969,887 | A | 11/1990 | Sodhi |
| 5,011,484 | A | 4/1991 | Breard |
| 5,047,055 | A | 9/1991 | Bao et al. |
| 5,059,193 | A | 10/1991 | Kuslich |
| 5,092,866 | A | 3/1992 | Breard et al. |
| 5,098,433 | A | 3/1992 | Freedland |
| 5,171,278 | A | 12/1992 | Pisharodi |
| 5,201,734 | A | 4/1993 | Cozad et al. |
| 5,290,312 | A | 3/1994 | Kojimoto et al. |
| 5,306,275 | A | 4/1994 | Bryan |
| 5,306,310 | A | 4/1994 | Siebels |
| 5,312,405 | A | 5/1994 | Korotko et al. |
| 5,360,430 | A | 11/1994 | Lin |
| 5,366,455 | A | 11/1994 | Dove |
| 5,390,683 | A | 2/1995 | Pisharodi |
| 5,395,370 | A | 3/1995 | Muller et al. |
| 5,401,269 | A | 3/1995 | Buttner-Janz et al. |
| 5,403,316 | A | 4/1995 | Ashman |
| 5,415,661 | A | 5/1995 | Holmes |
| 5,437,672 | A | 8/1995 | Alleyne |
| 5,437,674 | A | 8/1995 | Worcel et al. |
| 5,439,463 | A | 8/1995 | Lin |
| 5,454,812 | A | 10/1995 | Lin |
| 5,458,641 | A | 10/1995 | Ramirez Jimenez |
| 5,496,318 | A | 3/1996 | Howland et al. |
| 5,518,498 | A | 5/1996 | Lindenberg et al. |
| 5,554,191 | A | 9/1996 | Lahille et al. |
| 5,562,662 | A | 10/1996 | Brumfield et al. |
| 5,562,735 | A | 10/1996 | Margulies |
| 5,609,634 | A | 3/1997 | Voydeville |
| 5,609,635 | A | 3/1997 | Michelson |
| 5,628,756 | A | 5/1997 | Barker, Jr. et al. |
| 5,630,816 | A | 5/1997 | Kambin |
| 5,645,599 | A | 7/1997 | Samani |
| 5,653,762 | A | 8/1997 | Pisharodi |
| 5,653,763 | A | 8/1997 | Errico et al. |
| 5,658,335 | A | 8/1997 | Allen |
| 5,665,122 | A | 9/1997 | Kambin |
| 5,671,192 | A | 9/1997 | Schaffel |
| 5,674,295 | A | 10/1997 | Ray et al. |
| 5,676,702 | A | 10/1997 | Ratron |
| 5,685,826 | A | 11/1997 | Bonutti |
| 5,690,649 | A | 11/1997 | Li |
| 5,693,100 | A | 12/1997 | Pisharodi |
| 5,702,395 | A | 12/1997 | Hopf |
| 5,702,452 | A | 12/1997 | Argenson et al. |
| 5,702,455 | A | 12/1997 | Saggar |
| 5,707,390 | A | 1/1998 | Bonutti |
| 5,716,416 | A | 2/1998 | Lin |
| 5,723,012 | A | 3/1998 | Jeanson et al. |
| 5,725,341 | A | 3/1998 | Hofmeister |
| 5,746,762 | A | 5/1998 | Bass |
| 5,755,797 | A | 5/1998 | Baumgartner |
| 5,800,547 | A | 9/1998 | Schafer et al. |
| 5,810,815 | A | 9/1998 | Morales |
| 5,836,948 | A | 11/1998 | Zucherman et al. |
| 5,849,004 | A | 12/1998 | Bramlet |
| 5,860,977 | A | 1/1999 | Zucherman et al. |
| 5,888,196 | A | 3/1999 | Bonutti |
| 5,976,186 | A | 11/1999 | Bao et al. |
| 5,980,523 | A | 11/1999 | Jackson |
| 6,022,376 | A | 2/2000 | Assell et al. |
| 6,048,342 | A | 4/2000 | Zucherman et al. |
| 6,068,630 | A | 5/2000 | Zucherman et al. |
| 6,126,689 | A | 10/2000 | Brett |
| 6,126,691 | A | 10/2000 | Kasra et al. |
| 6,127,597 | A | 10/2000 | Beyar et al. |
| 6,132,464 | A | 10/2000 | Martin |
| 6,190,413 | B1 | 2/2001 | Sutcliffe |
| 6,190,414 | B1 | 2/2001 | Young |
| 6,214,050 | B1 | 4/2001 | Huene |
| 6,293,949 | B1 | 9/2001 | Justis et al. |
| 6,336,930 | B1 | 1/2002 | Stalcup et al. |
| 6,348,053 | B1 | 2/2002 | Cachia |
| 6,352,537 | B1 | 3/2002 | Strnad |
| 6,364,883 | B1 | 4/2002 | Santilli |
| 6,371,987 | B1 | 4/2002 | Weiland et al. |
| 6,375,682 | B1 | 4/2002 | Fleischmann et al. |
| 6,402,750 | B1 | 6/2002 | Atkinson et al. |
| 6,402,751 | B1 | 6/2002 | Hoeck et al. |
| 6,419,704 | B1 | 7/2002 | Ferree |
| 6,440,169 | B1 | 8/2002 | Elberg et al. |
| 6,447,513 | B1 | 9/2002 | Griggs |
| 6,451,019 | B1 | 9/2002 | Zucherman et al. |
| 6,500,178 | B2 | 12/2002 | Zucherman et al. |
| 6,514,256 | B2 | 2/2003 | Zucherman et al. |
| 6,520,991 | B2 | 2/2003 | Huene |
| 6,554,833 | B2 | 4/2003 | Levy |
| 6,582,433 | B2 | 6/2003 | Yun |
| 6,582,467 | B1 | 6/2003 | Teitelbaum et al. |
| 6,592,585 | B2 | 7/2003 | Lee et al. |
| 6,626,944 | B1 | 9/2003 | Taylor |
| 6,645,207 | B2 | 11/2003 | Dixon et al. |
| 6,685,742 | B1 | 2/2004 | Jackson |
| 6,695,842 | B2 | 2/2004 | Zucherman et al. |
| 6,709,435 | B2 | 3/2004 | Lin |
| 6,723,126 | B1 | 4/2004 | Berry |
| 6,730,126 | B2 | 5/2004 | Boehm, Jr. et al. |
| 6,733,534 | B2 | 5/2004 | Sherman |
| 6,736,818 | B2 | 5/2004 | Perren et al. |
| 6,743,257 | B2 | 6/2004 | Castro |
| 6,758,863 | B2 | 7/2004 | Estes et al. |
| 6,761,720 | B1 | 7/2004 | Senegas |
| 6,770,096 | B2 | 8/2004 | Bolger et al. |
| 6,783,530 | B1 | 8/2004 | Levy |
| 6,835,205 | B2 | 12/2004 | Atkinson et al. |
| 6,905,512 | B2 | 6/2005 | Paes et al. |
| 6,946,000 | B2 | 9/2005 | Senegas et al. |
| 6,981,975 | B2 | 1/2006 | Michelson |
| 7,011,685 | B2 | 3/2006 | Arnin et al. |
| 7,041,136 | B2 | 5/2006 | Goble et al. |
| 7,048,736 | B2 | 5/2006 | Robinson et al. |

| | | |
|---|---|---|
| 7,081,120 B2 | 7/2006 | Li et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 2001/0016743 A1 | 8/2001 | Zucherman et al. |
| 2001/0020186 A1* | 9/2001 | Boyce et al. ............. 623/17.16 |
| 2002/0099444 A1 | 7/2002 | Boyd et al. |
| 2002/0143331 A1 | 10/2002 | Zucherman et al. |
| 2003/0014114 A1 | 1/2003 | Ralph et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0087947 A1 | 5/2004 | Lim et al. |
| 2004/0097931 A1 | 5/2004 | Mitchell |
| 2004/0133204 A1 | 7/2004 | Davies |
| 2004/0133280 A1 | 7/2004 | Trieu |
| 2004/0167625 A1 | 8/2004 | Beyar et al. |
| 2004/0199255 A1 | 10/2004 | Mathieu et al. |
| 2004/0260397 A1 | 12/2004 | Lambrecht et al. |
| 2005/0004573 A1 | 1/2005 | Abdou |
| 2005/0010293 A1 | 1/2005 | Zucherman et al. |
| 2005/0049708 A1 | 3/2005 | Atkinson et al. |
| 2005/0085814 A1 | 4/2005 | Sherman et al. |
| 2005/0143738 A1 | 6/2005 | Zucherman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 | 11/2005 | Trieu |
| 2005/0273166 A1 | 12/2005 | Sweeney |
| 2005/0288672 A1 | 12/2005 | Ferree |
| 2006/0004447 A1* | 1/2006 | Mastrorio et al. ........ 623/17.11 |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1* | 5/2006 | Lins ............................. 606/90 |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0183218 A1 | 8/2006 | Takahashi et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0195191 A1 | 8/2006 | Sweeney et al. |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0032790 A1 | 2/2007 | Aschmann et al. |
| 2007/0043362 A1 | 2/2007 | Malandain et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0183211 A1 | 7/2008 | Lamborne et al. |
| 2008/0215094 A1 | 9/2008 | Taylor |
| 2008/0221685 A9 | 9/2008 | Altarac et al. |
| 2008/0262617 A1 | 10/2008 | Froehlich et al. |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105773 A1 | 4/2009 | Lange et al. |
| 2009/0234389 A1 | 9/2009 | Chuang et al. |

| | | | |
|---|---|---|---|
| 2009/0270918 A1 | 10/2009 | Attias et al. | |
| 2010/0121379 A1 | 5/2010 | Edmond | |

FOREIGN PATENT DOCUMENTS

| | | |
|---|---|---|
| DE | 3922044 A1 | 2/1991 |
| DE | 4012622 C1 | 7/1991 |
| DE | 102005005694 A1 | 8/2006 |
| EP | 0322334 B1 | 2/1992 |
| EP | 0767636 B1 | 1/1999 |
| EP | 1004276 A1 | 5/2000 |
| EP | 1138268 A1 | 10/2001 |
| EP | 1302169 A1 | 4/2003 |
| EP | 1330987 A1 | 7/2003 |
| EP | 1854433 A1 | 11/2007 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| SU | 988281 | 1/1983 |
| SU | 1484348 A1 | 6/1989 |
| WO | WO 94/26192 | 11/1994 |
| WO | WO 94/26195 | 11/1994 |
| WO | 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084768 A2 | 10/2004 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | 2006064356 | 6/2006 |
| WO | WO 2006/064356 A1 | 6/2006 |
| WO | 2006102269 | 9/2006 |
| WO | WO 2007/034516 A1 | 3/2007 |
| WO | WO 2007052975 A1 | 5/2007 |
| WO | 2009/083276 A1 | 7/2009 |
| WO | 2009/083583 A1 | 7/2009 |
| WO | 2009/098536 A1 | 8/2009 |

OTHER PUBLICATIONS

"Tecnica Operatoria Per II Posizionamento Della Protesi DIAM," date unknown, pp. 1-3.

"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, "Analysis of Clinical Experience with a Posterior Shock-Absorbing Implant," date unknown, pp. 2-9.

Cousin Biotech, Dispositif Intervertébral Amortissant, Jun. 1998, pp. 1-4.

Cousin Biotech, Technique Operatoire de la Prothese DIAM, date unknown, Annexe 1, pp. 1-8.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," Spine, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," Spine, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," Spine, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," Spine, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," Spine, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maiîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èrnes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

* cited by examiner

SPINAL IMPLANT SYSTEM

TECHNICAL FIELD

The present invention relates generally to the field of surgery and medical implants, and more particularly, to spinal implant systems and methods for inserting spinal implant systems.

BACKGROUND OF THE INVENTION

The human spine is a biomechanical structure with thirty-three vertebral members, and is responsible for protecting the spinal cord, nerve roots and internal organs of the thorax and abdomen. The spine also provides structural support for the body while permitting flexibility of motion. A significant portion of the population will experience back pain at some point in their lives resulting from a spinal condition. The pain may range from general discomfort to disabling pain that immobilizes the individual. Back pain may result from a trauma to the spine, be caused by the natural aging process, or may be the result of a degenerative disease or condition.

Procedures to remedy back problems sometimes require correcting the distance between vertebral members by inserting an intervertebral device (e.g., spacer) between the members. Dynamic interspinous spacers are currently used to treat patients with a variety of indications. Essentially, these patients present a need for distraction of the posterior elements (e.g., the spinous processes) of the spine using a mechanical device. Current clinical indications for such a device may include stenosis, disc herniation, facet arthropathy, degenerative disc disease and adjacent segment degeneration.

Currently, marketed interspinous devices include rigid and flexible spacers made from PEEK, titanium, silicone or some combination of other implantable materials. However, these devices require an open technique to be implanted, and many require destroying important anatomical stabilizers, such as the supraspinous ligament. In particular, the current technique for placing such spacers between the interspinous processes is to cut the interspinous and supraspinous ligaments and slide the device over the adjacent spinous processes.

Thus, a need exists for improved spinal implant systems and methods for implanting such systems which are minimally invasive and minimally destructive of important anatomical stabilizers. The systems and methods disclosed herein address this need.

SUMMARY OF THE INVENTION

The shortcomings of the prior art are overcome and additional advantages are provided in one aspect through an interspinous spacer system which includes a core shaped and configured to fit in an interspinous space between adjacent spinous processes. A plurality of extending forks extends from the core and has shapes configured to extend along the vertical sides of the spinous processes. A first fork of the plurality of forks is moveable relative to the core from a non-use position to an in-use position. The first fork is located on a first side of the core when in the in-use position and has a first inner side bounding an opening for receiving a first spinous process of the spinous processes. The first fork is substantially non-flexible. A second fork is located on the first side of the core and the second fork has a second inner side bounding the opening for receiving the first spinous process of the spinous processes. The second fork is immovable relative to the core. The first fork avoids protruding from the core such that the first fork bounds the opening in the non-use position to allow the core to be inserted into the interspinous space in the non-use position to avoid damage to a supraspinous ligament adjacent the space.

The present invention provides, in a further aspect, an interspinous spacer system which includes a core having a shape configured to fit between adjacent spinous processes. A plurality of extending forks extends from the core and has shapes configured to extend along vertical sides of the spinous processes. A first fork and second fork of the plurality of forks are coupled to the core and moveable from a non-use position to an in-use position. The first fork and the second fork define an opening for receiving a first spinous process of the spinous processes when in an in-use position. The core includes a cavity defined by inner surfaces of the core and the cavity includes a cavity width between the inner surfaces of the core defining the cavity. A distance between opposite longitudinal outermost surfaces of the first fork and the second fork is less than the cavity width to allow the first fork and the second fork to be received in the cavity in the non-use position to avoid damaging a supraspinous process adjacent the space.

The present invention provides, in yet another aspect, a method for spacing adjacent spinous processes which includes providing an interspinous spacer having a non-use position and an in-use position. The spacer includes a core and a plurality of extending of forks extending from the core and having shapes configured to extend along vertical sides of the spinous processes. The plurality of forks includes a first fork and a second fork. The first fork avoids protruding from the core such that the first fork avoids bounding an opening for receiving the first spinous process of the spinous processes in the non-use position. The first fork is substantially non-flexible. The second fork is located on a first side of the core and has an inner side bounding the opening for receiving the first spinous process of the spinous processes and is immovable relative to the core. The core is inserted, when the interspinous spacer is in the non-use position, into a space between the spinous processes from a side of a mid-line of a spine of a patient to avoid damaging a supraspinous ligament adjacent the space. The first fork is moved from the non-use position to the in-use position such that the first fork is located on the first side of the core. The fork has a first inner side bounding the opening for receiving the first spinous process of the spinous processes in the in-use position.

The present invention provides, in yet a further aspect, a method for spacing adjacent spinous processes which includes providing an interspinous spacer having a non-use position and an in-use position. The spacer includes a core and a plurality of extending forks extending from the core having shapes configured to extend along vertical sides of the spinous processes. The core is inserted, when the spacer is in the non-use position, into a space between the spinous processes from a side of a mid-line of a spine of a patient to avoid damaging a supraspinous ligament adjacent the space. The spacer is moved from the non-use position to the in-use position such that a first fork and a second fork of the plurality of forks coupled to the core define an opening receiving a first spinous process of the spinous processes in the in-use position. The moving includes extending the first fork and the second fork from a cavity of the core with the cavity being defined by inner surfaces of the core. The cavity has a cavity width between the inner surfaces. A distance between opposite longitudinal outer most surfaces of the first fork and the second fork is less than the cavity width to allow the first fork and the second fork to be received in the cavity in the non-use position.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention will be apparent from the following detailed description of preferred embodiments taken in conjunction with the accompanying drawings in which:

BEST MODE FOR CARRYING OUT THE INVENTION

In accordance with the principles of the present invention, spinal implant systems and methods for inserting spinal implants are provided. The implants described herein avoid some or all of the cuts to a supraspinous ligament of a patient by allowing the implants to be inserted from a side of the patient's spine, interspinous space and supraspinous ligament when the implant is configured in a non-use position. The in-situ implant may then be manipulated to an in-use position by a surgeon from the same side as the insertion of the implant without damaging the supraspinous ligament. For example, the implant may be inserted, and manipulated, from a side of a mid-line of a patient's spine when viewed from a posterior thereof.

Figure 1:
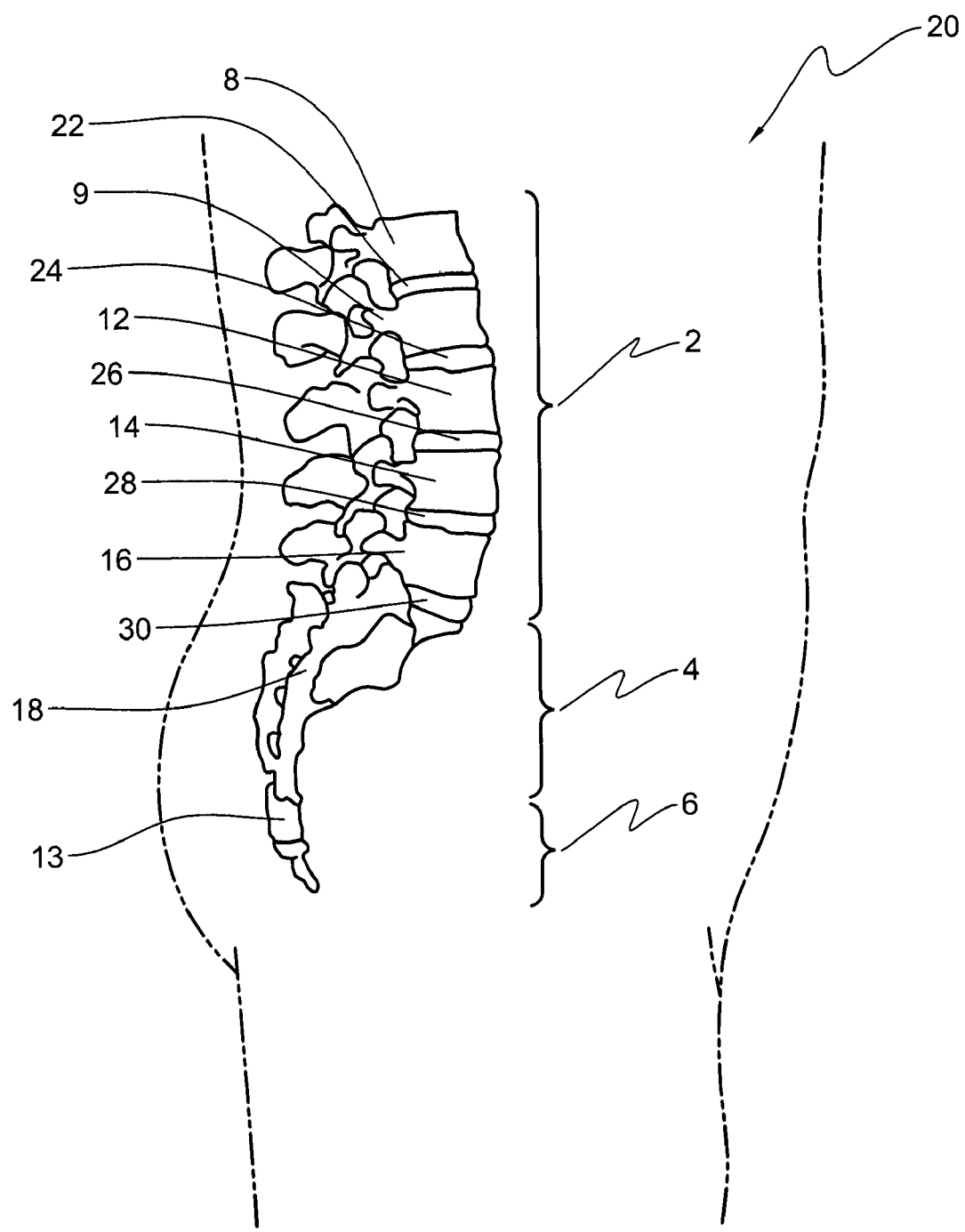
FIG. 1 is a side elevational view of a lower portion of a spine of a human, in accordance with an aspect of the present invention.

Referring to FIG. 1, a portion of a spinal column 20 is shown. As depicted, spinal column 20 includes a lumbar region 2, a sacral region 4, and a coccygeal region 6. As is known in the art, column 20 also includes a cervical region and a thoracic region. For clarity and ease of discussion, the cervical region and the thoracic region are not illustrated. Lumbar region 2 includes a first lumbar vertebra 8, a second lumbar vertebra 9, a third lumbar vertebra 12, a fourth lumbar vertebra 14, and a fifth lumbar vertebra 16. Sacral region 4 includes a sacrum 18. Further, coccygeal region 6 includes a coccyx 13.

As depicted in FIG. 1, a first intervertebral lumbar disc 22 is disposed between first lumbar vertebra 8 and second lumbar vertebra 9. A second intervertebral lumbar disc 24 is disposed between second lumbar vertebra 9 and third lumbar vertebra 12. A third intervertebral lumbar disc 26 is disposed between third lumbar vertebra 12 and fourth lumbar vertebra 14. Further, a fourth intervertebral lumbar disc 28 is disposed between fourth lumbar vertebra 14 and fifth lumbar vertebra 16. Additionally, a fifth intervertebral lumbar disc 30 is disposed between fifth lumbar vertebra 16 and sacrum 18.

Figure 2:
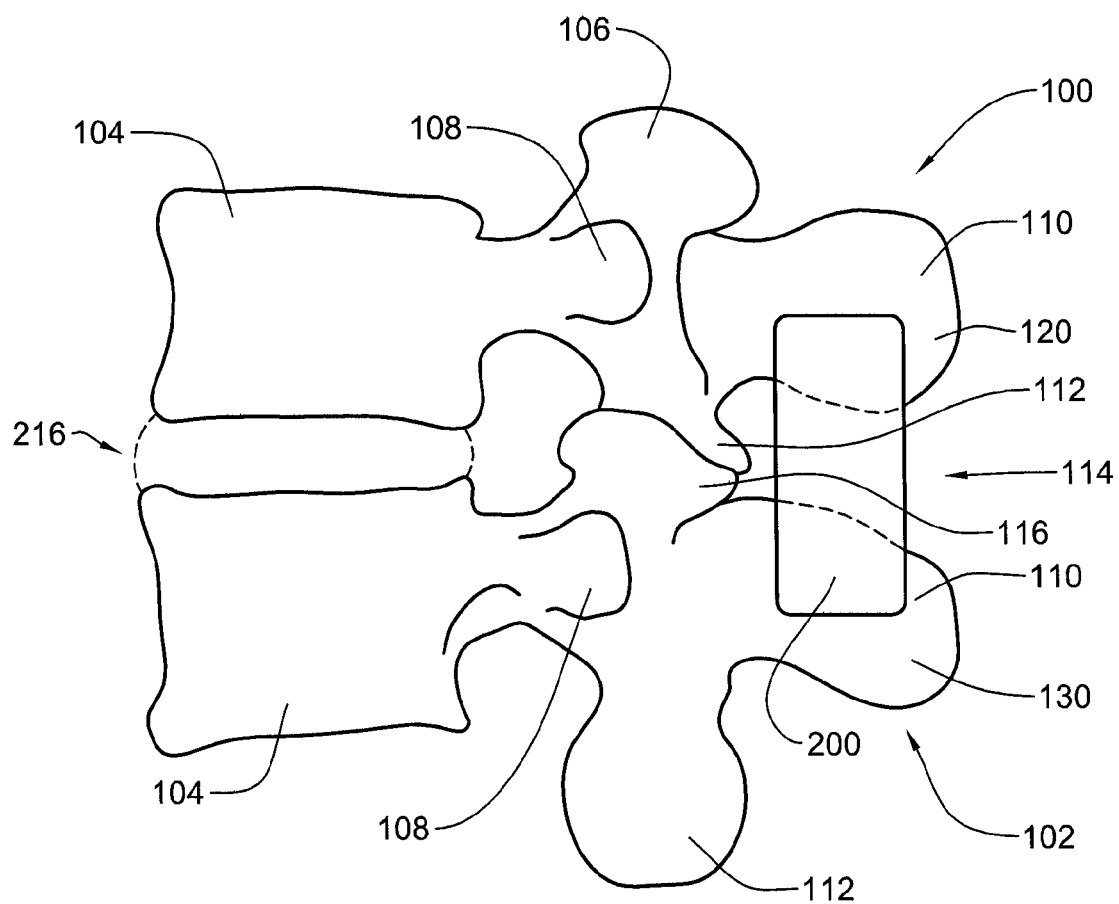
FIG. 2 is a side elevational view of two vertebrae of the spine of FIG. 1 having a spinal implant between spinous processes thereof, in accordance with an aspect of the present invention.

FIG. 2 depicts a lateral view of two adjacent vertebrae, e.g., two of the lumbar vertebra 8, 9, 12, 14, 16 shown in FIG. 1. FIG. 2 illustrates a superior vertebra 100 and an inferior vertebra 102 with a lumbar disc 216 therebetween. As shown, each vertebra 100, 102 includes a vertebral body 104, a superior articular process 116, a transverse process 108, a spinous process 110 and an inferior articular process 112. FIG. 2 further depicts an interspinous space 114 that can be established between an upper spinous process 120 and a lower spinous process 130 by the removal of the interspinous ligament and any other boney or soft tissue needed for the insertion of a spinal implant 200.

Figure 3:
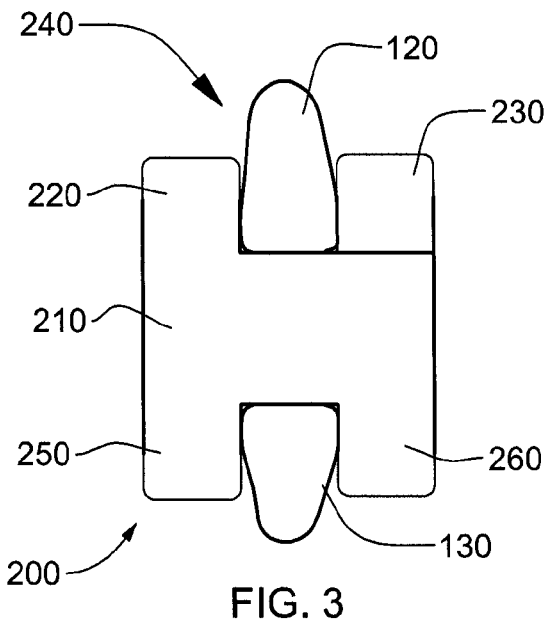
FIG. 3 is a front elevational view of the spinal implant and spinous processes of FIG. 2, in accordance with an aspect of the present invention.

As depicted in FIG. 3, a spinal implant 200 may be H-shaped including a core 210 and a plurality of extending forks extending away from the core. A first fork 220 and a second fork 230 extend upwardly from core 210, define an opening 240 to receive upper spinous process 120, and are configured (e.g., shaped and dimensioned) to be received on opposite sides of upper spinous process 120. A third fork 250 and a fourth fork 260 extend downwardly away from core 210 and are configured (e.g., shaped and dimensioned) to be received on opposite sides of lower spinous process 130. Core 210 is configured (e.g., shaped and dimensioned) to be received between upper spinous process 120 and lower spinous process 130 and to provide support, distraction and/or separation pressure therebetween. For example, core 210 may maintain a space between upper spinous process 120 and lower spinous process 130 in an area between the processes where an interspinous ligament has been removed. Further, core 210 may maintain such support, distraction and/or separation pressure to remove or off load at least some pressure from articular processes 112 and 116.

Figure 4:
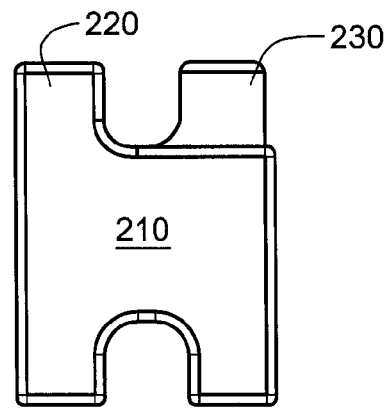
FIG. 4 is a front elevational view of a spinal implant, in accordance with an aspect of the present invention.
Figure 5:
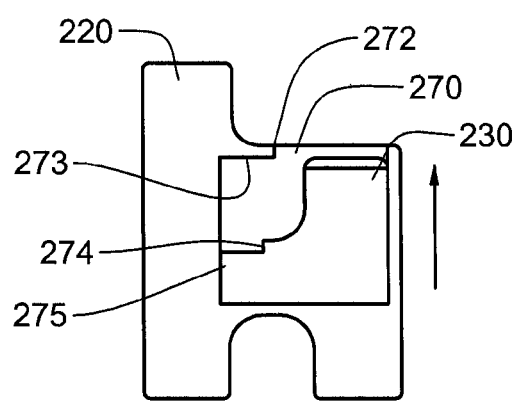
FIG. 5 is a front cross-sectional view of the implant of FIG. 4, with an extending fork thereof located in a cavity thereof, in accordance with an aspect of the present invention.
Figure 6:
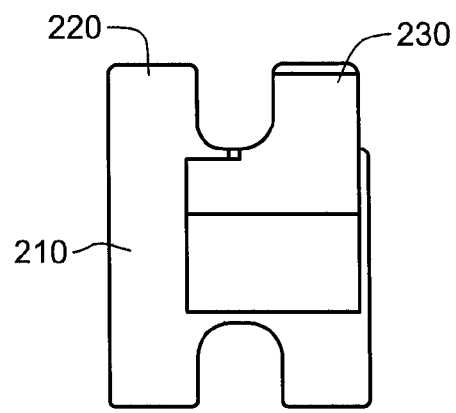
FIG. 6 is a front cross-sectional view of the implant of FIG. 4, with the extending fork protruding from the cavity, in accordance with an aspect of the present invention.

As depicted in FIGS. 4-6, second fork 230 may be received in a cavity 270 of implant 200 when implant 200 is in a non-use position, and first fork 220 and core 210 may bound opening 240 having substantially an L-shape, prior to the insertion of implant 200 into an interspinous cavity. After such insertion, second fork 230 may be extended upwardly (i.e., to an in-use position) such that second fork 230 and first fork 220 bound opening 240 (e.g., having substantially a U-shape) receiving upper spinous process 120. Second fork 230 may be held in place via a friction fit between an engaging portion 272 of core 210 and a corresponding engaging portion 274 of second fork 230 when second fork 230 is "snapped into" the remainder of implant 200. Also, an extending portion 275 of fork 230 may abut a bottom side 273 of engagement portion 272 to inhibit vertical movement of fork 230 out of cavity 270. Alternatively, second fork 230 may be held in place utilizing a set screw, ratcheting mechanism, shim, spring, or any other means of holding second fork 230 in place and inhibiting separation of second fork 230 from the remainder of implant 200. The use of set screws, ratcheting mechanisms, springs and shims are further discussed below.

Figure 7:
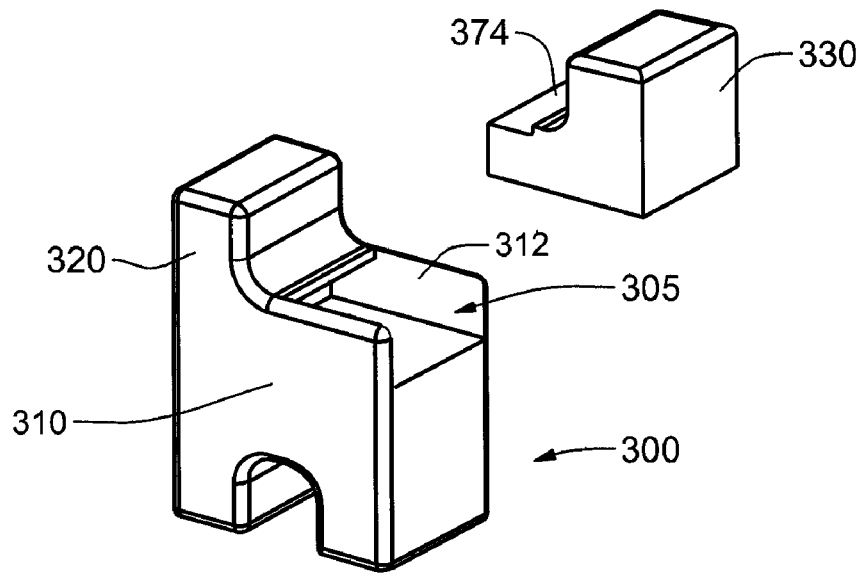
FIG. 7 is a perspective view of a spinal implant, in accordance with an aspect of the present invention.
Figure 8:
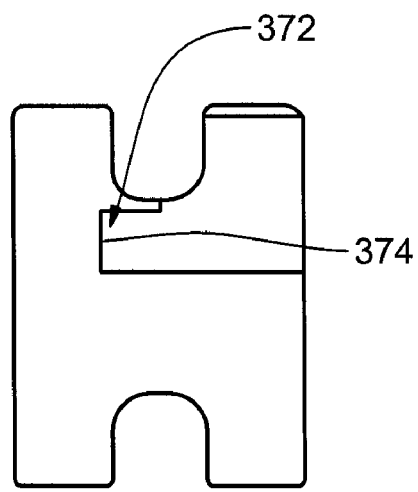
FIG. 8 is a front cross-sectional view of the implant of FIG. 7, in accordance with an aspect of the present invention.
Figure 9:
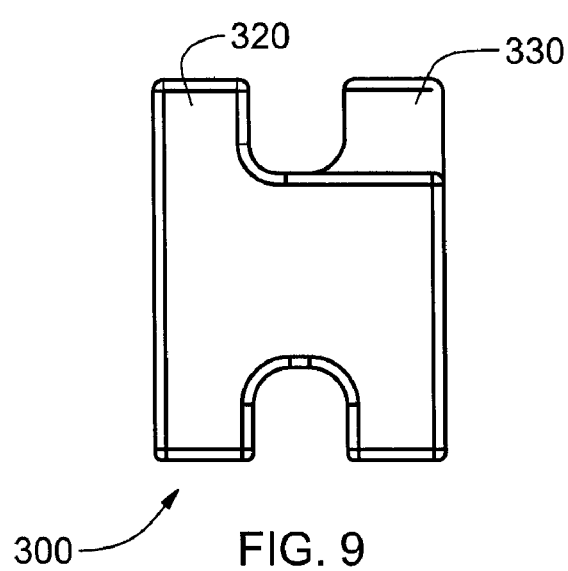
FIG. 9 is a front elevational view of the implant of FIG. 7, in accordance with an aspect of the present invention.

As depicted in FIGS. 7-9, another example includes an implant 300 having a first fork 330 separate from, and attachable to, a core 310. Implant 300 may include a cavity 305 configured (i.e., shaped and dimensioned) to receive first fork 330. First fork 330 may be held in place via a friction fit between walls 312 defining an internal cavity engaging portion 372 of a core 310 and a corresponding connecting portion 374 of first fork 330 when first fork 330 is "snapped into" the remainder of implant 300. Connecting portion 374 and engaging portion 372 may inhibit movement of fork 330 away from core 310. In one example, first fork 330 and/or core 310 may be sufficiently flexible to allow the insertion of connecting portion 374 into engaging portion 372 such that friction therebetween inhibits separation after they are connected. Alternatively, first fork 330 may be held in place utilizing a set screw, ratcheting mechanism, shim, spring, or any other means of holding first fork 330 in place.

Figure 10:
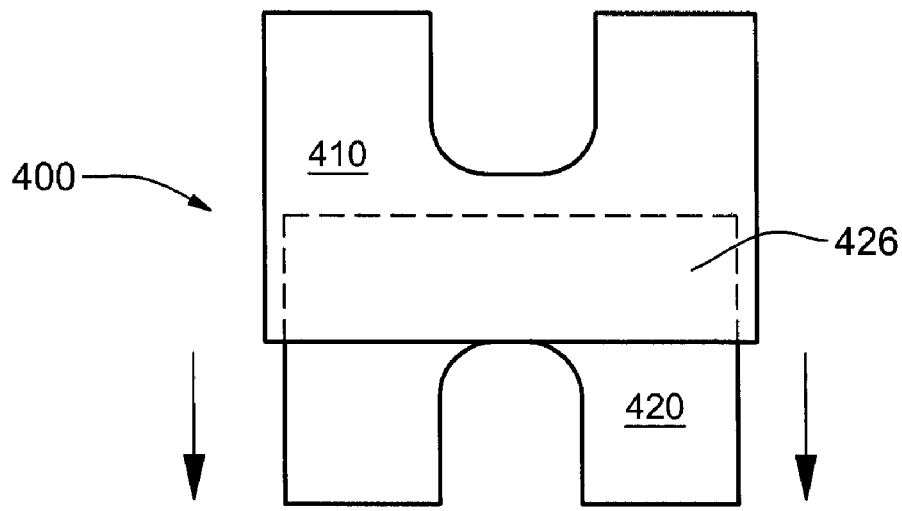
FIG. 10 is a front elevational view of an implant in a non-use position, in accordance with an aspect of the present invention.
Figure 11:
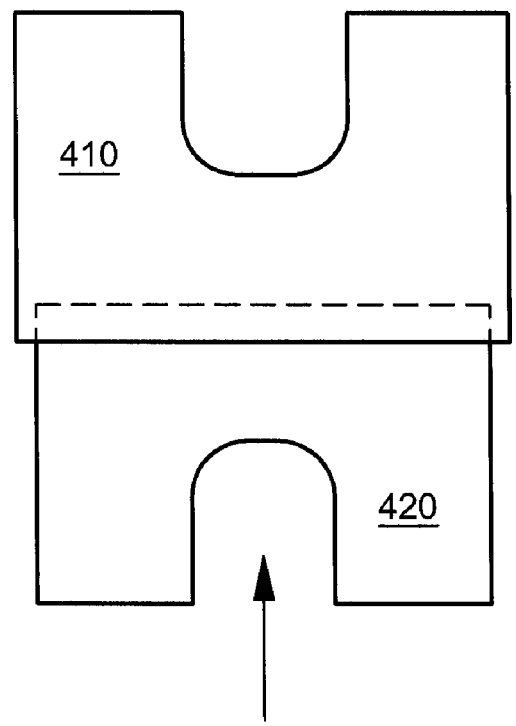
FIG. 11 is a front elevational view of the implant of FIG. 10 in an in-use position, in accordance with an aspect of the present invention.
Figure 12:
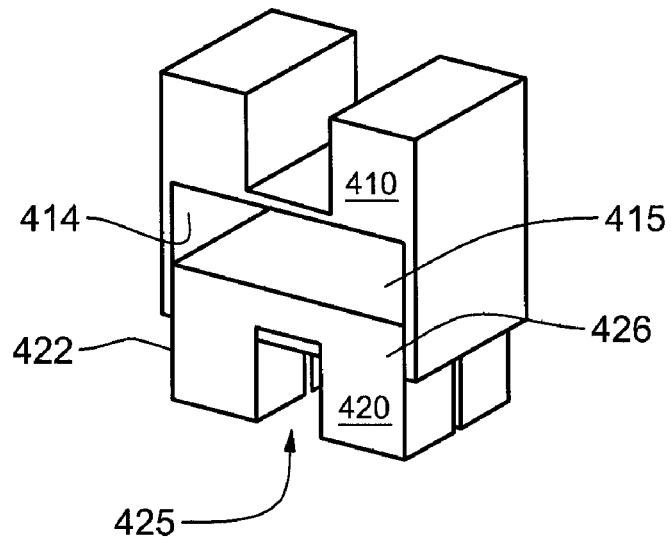
FIG. 12 is a front cross-sectional view of the implant of FIG. 10, in accordance with an aspect of the present invention.
Figure 13:
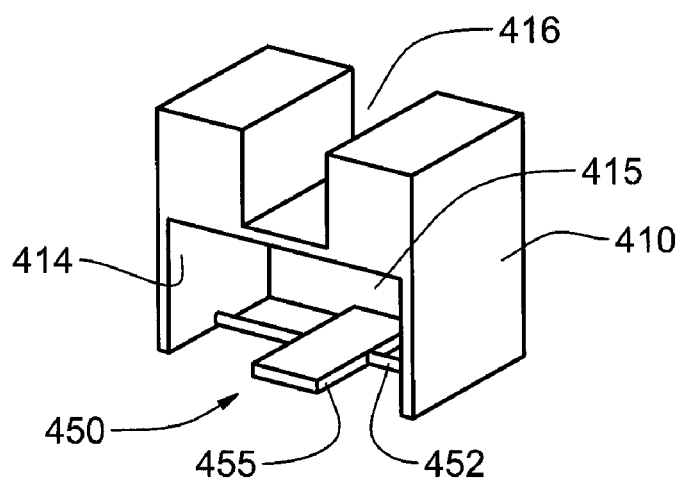
FIG. 13 is an exploded cross-sectional view of the implant of FIG. 10, in accordance with an aspect of the present invention.
Figure 13:
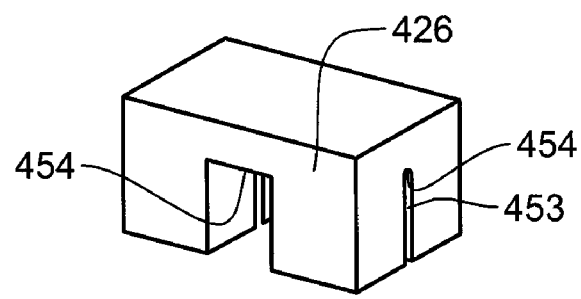

As depicted in FIGS. 10-13 in a further example, an implant 400 includes a top member 410 movably attached to a bottom member 420. In a non-use position depicted in FIG. 10, a top portion 426 of bottom member 420 is received in a cavity 415 (FIG. 12) of top member 410. The cavity is configured (e.g., shaped and dimensioned) to receive bottom member 420. For example, cavity 415 is defined by inner surfaces 414 of top member 410 such that the width of bottom member 420 is less than the width of inner surfaces 414 and thus cavity 415 as depicted in FIGS. 12-13. When in use top member 410 and bottom member 420 may be vertically expanded relative to one another such that a minimal amount of top portion 426 of bottom member 420 is received within cavity 415 and implant 400 may be at its maximum height as depicted in FIG. 11. Thus, implant 400 may have its height minimized in a non-use position as depicted in FIG. 10 to allow it to be fit into an interspinous space (e.g., space 114) between spinous processes, and implant 400 may then be expanded or increased in height as desired, i.e., to an in-use position.

Top member 410 may be held in place via a friction fit between an engaging portion, such as inner surfaces 414 of cavity 415, and a corresponding engaging surface, such as outer portion 422, of bottom member 420 when top member 410 and bottom member 420 are extended to a desired height relative to one another. Alternatively, top member 410 and bottom member 420 may be held in place relative to each other utilizing a set screw, ratcheting mechanism, shim, spring, or any other means of holding top member 410 and bottom member 420 at a fixed position relative to each other.

Top member 410 may also include a retaining member 450 configured to retain bottom member 420 connected to top member 410. Retaining member 450 may include a connecting member or rod 452 connected to opposite inner surfaces 414 of cavity 415 of top member 410 and may be received in passages 453 of bottom member 420 when bottom member 420 is received in cavity 415. Rod 452 may be connected to a holder 455 which is configured (e.g., shaped and dimensioned) to be received in a cavity 425 configured to receive a lower spinous process (e.g., lower spinous process 130). Retaining member 450 thus allows movement of bottom member 420 into cavity 415 but inhibits movement of bottom member 420 past retaining member 450 in a direction out of the cavity by contact of holder 455 and rod 452 with upper surfaces 454 of bottom member 420. Also, as noted above, top member 410 and bottom member 420 may be held relative to one another without using retaining member 450 (e.g., via a friction fit, set screw, ratcheting mechanism, shim, spring, or other means of holding top and bottom members relative to each other). Top member 410 also includes an opening 416 for receiving an upper spinous process (e.g., upper spinous process 120).

Figure 14:
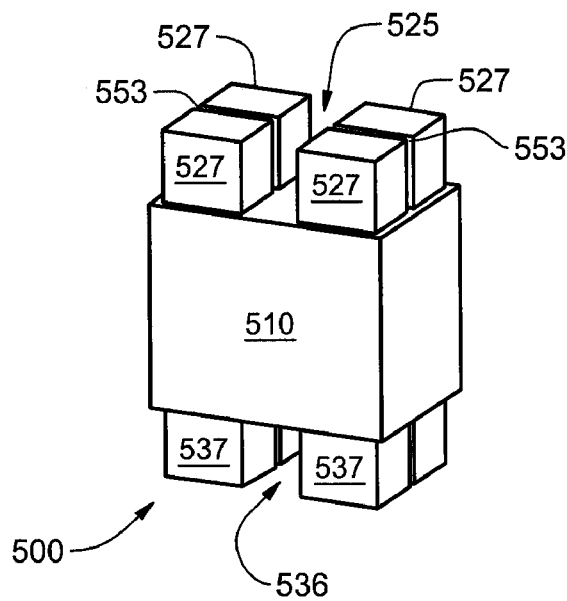
FIG. 14 is a front perspective view of an implant in an in-use position, in accordance with an aspect of the present invention.
Figure 15:
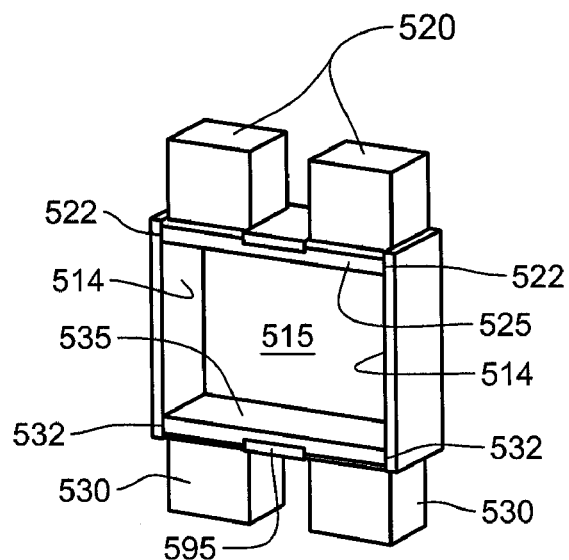
FIG. 15 is a front cross-sectional view of the implant of FIG. 14, in accordance with an aspect of the present invention.
Figure 16:
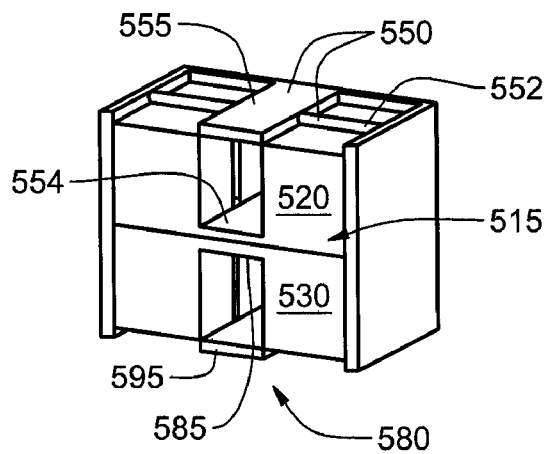
FIG. 16 is a front cross-sectional view of the implant of FIG. 14 in a non-use position, in accordance with an aspect of the present invention.

In another example depicted in FIGS. 14-16, an implant 500 may include a core 510 having a cavity 515 configured (e.g., shaped and dimensioned) to receive a top member 520 and a bottom member 530 therein when in a non-use position. For example, in the non-use position depicted in FIG. 16, top member 520 and bottom member 530 may be received within cavity 515 to allow implant 500 to be inserted into an interspinous cavity such as interspinous cavity 114 (FIG. 2) while minimizing damage to a supraspinous ligament. After insertion into such an interspinous cavity, top member 520 and bottom member 530 may be vertically separated from one another (e.g., using a spring or other biasing mechanism) as depicted in FIGS. 14-15. In this position, an upper spinous process (e.g., upper spinous process 120 (FIG. 3)) may be received in an upper spinous cavity 525 between upper forks 527 and a lower spinous process (e.g., lower spinous process 130 (FIG. 3)) may be received in a lower spinous cavity 535 between lower forks 537.

For example, cavity 515 is defined by inner surfaces 514 of core 510 such that the widths of top member 520 and bottom member 530 are less than the distance between inner surfaces 514 defining cavity 515. When in use top member 520 and bottom member 530 may be vertically expanded relative to one another such that a minimal amount of top portion 535 of bottom member 530 and bottom portion 525 of top member 510 are received within cavity 515 and implant 500 may be at its maximum height as depicted in FIGS. 14-15. Thus, implant 500 may have its height minimized in a non-use position as depicted in FIG. 16 to allow it to be easily fit into the interspinous space (e.g., space 114) between the spinous processes and implant 500 may then be expanded or increased in height as desired, i.e., to an in-use position.

Top member 520 and bottom member 530 may be held in place relative to core 510 in an in-use or a non-use position via a friction fit between an engaging portion, such as outer surfaces 522, of top member 520 and an engaging portion, such as outer surfaces 532, of bottom member 530 with a corresponding engaging portion and/or inner surfaces 514 of core 510. Alternatively, top member 520 and bottom member 530 may be held in place relative to each other and core 510 utilizing a set screw, ratcheting mechanism, shim, spring or any other means of holding top member 520 and bottom member 530 relative to core 510 and each other.

Core 510 may also include a top retaining member 550 configured to retain top member 520 connected to core 510. Retaining member 550 may include a connecting member, such as a rod 552, connected to opposite inner surfaces 514 of cavity 515 of core 510 and may be received in passages 553 between upper forks 527 of top member 520 when top member 520 is received in cavity 515. Rod 550 may be connected to a holder 555 which is configured (e.g., shaped and dimensioned) to be received in cavity 525 configured to receive an upper spinous process (e.g., upper spinous process 120). Retaining member 550 thus allows movement of top member 520 into cavity 515 but inhibits movement of top member 520 past retaining member 550 in a direction out of the cavity by contact of holder 555 and rod 552 with upper surfaces 554 of top member 520. Similarly, a bottom retaining member 580 inhibits movement of bottom member 530 away from cavity 515 by contact between bottom surfaces 585 of bottom member 530 with a holder 595 connected to inner surfaces 514 by a rod (not shown). Also, as noted above, top member 520 and bottom member 530 may be held in place relative to core 510 in an in-use, or non-use position without utilizing top retaining member 550 or bottom retaining member 580 (e.g., via a friction fit, set screw, ratcheting mechanism, shim, spring, or other means of holding top and bottom members relative to each other).

Figure 17:
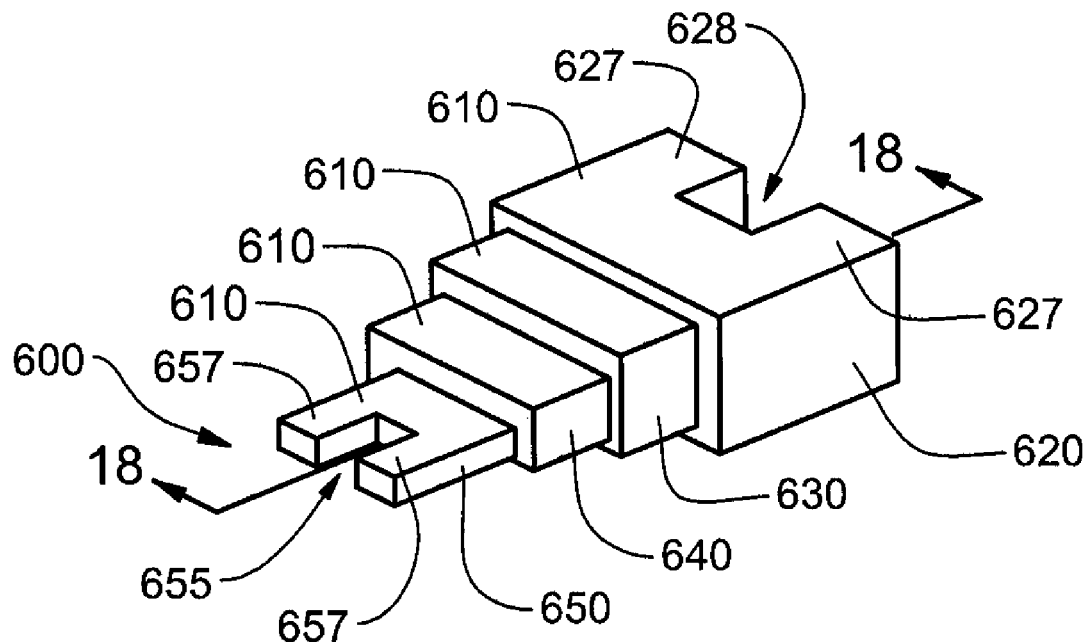
FIG. 17 is a perspective view of a spinal implant, in accordance with an aspect of the present invention.
Figure 18:
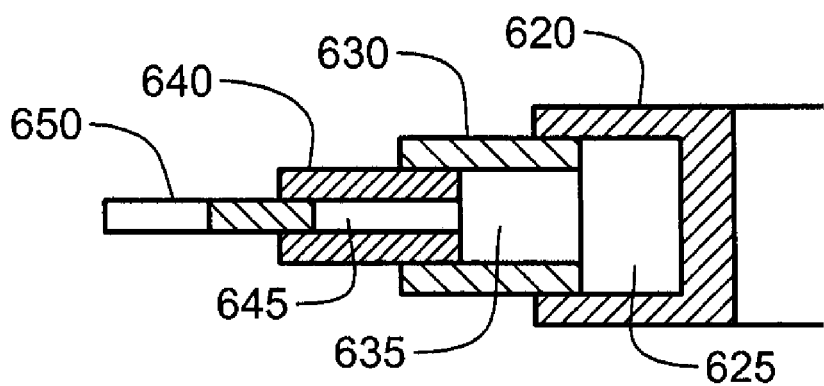
FIG. 18 is a front cross-sectional view of the implant of FIG. 17, in accordance with an aspect of the present invention.

In another example depicted in FIGS. 17-18, an implant 600 includes a plurality of telescoping sections 610. A first section 620 has a cavity 625 which may at least partially receive a second section 630 therein. A third section 640 may be at least partially received in a cavity 635 of second section 630. A fourth section 650 may be received at least partially in a cavity 645 of third section 640. Each section may be received in the appropriate cavity of the section connected thereto when in a non-use position, i.e. prior to insertion of implant 600 into an interspinous cavity such as interspinous cavity 114 (FIG. 2). Adjacent sections may then be held relative to one another in an in-use position, as depicted for example in FIGS. 17-18, by a friction fit, set screw, ratcheting mechanism, spring(s), or any other means of holding the sections relative to one another such that they may maintain an upper spinous process (e.g. upper spinous process 120 (FIG. 2)) and a lower spinous process (lower spinous process 130 (FIG. 2)) at a desired position relative to one another. As depicted, fourth section 650 may include a cavity 655 for receiving a spinous process, which is bounded by forks 657, and first section 620 may include a cavity 625 for receiving an opposite spinous process, which is bounded by forks 627.

Figure 19:
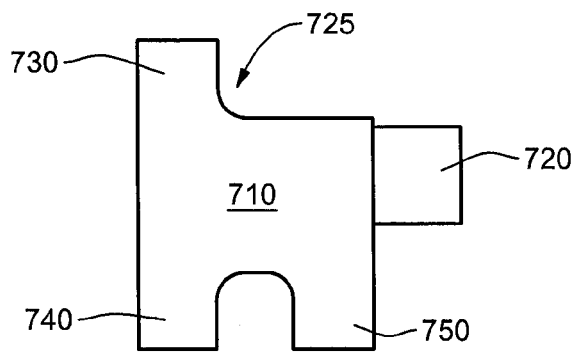
FIG. 19 is a front elevational view of a spinal implant in a non-use position, in accordance with an aspect of the present invention.
Figure 20:
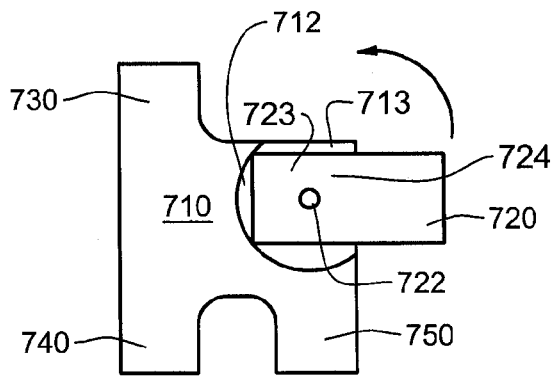
FIG. 20 is a front cross-sectional view of the implant of FIG. 19, in accordance with an aspect of the present invention.
Figure 21:
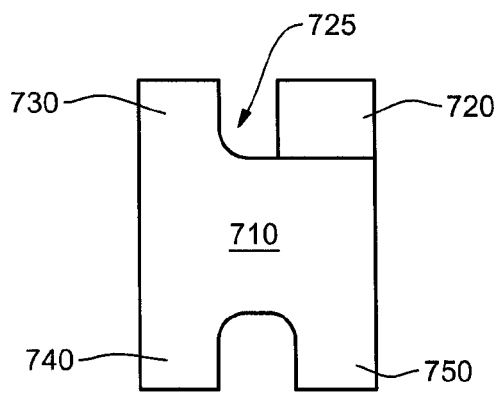
FIG. 21 is a front elevational view of the implant of FIG. 19 in an in-use position, in accordance with an aspect of the present invention.

As depicted in FIGS. 19-21, an implant 700 may include a fork 720 rotatably attached to a core 710. Fork 720 may be movable (e.g., rotatable about a pin 722) from a first (i.e., non-use) position in which the implant includes an h-shape, as depicted in FIGS. 19 and 20 to a second (i.e., in-use) position depicted in FIG. 21 in which the implant is H-shaped. An internal end 723 of fork 720 may be received in a cavity 712 of core 710 and cavity 712 may be formed in an arc shape to allow such rotation as depicted in FIG. 20. Fork 720 may have a rectilinear cross-section as depicted in the figures, for example.

Fork 720 may be located in a non-use position in the first position which may facilitate the insertion of the implant into an interspinous space such as interspinous space 114 (FIG. 2). For example, the offset position of fork 720 in FIGS. 19-20 may allow the implant to be manipulated under or around the supraspinous ligament to avoid (or minimize) the necessity of cutting such ligament. When in the in-use position depicted in FIG. 21, fork 720 and a second fork 730 may be substantially parallel to each other and may bound an opening 725 for receiving an upper spinous process such as upper spinous process 120 (FIG. 2). Core 710, second fork 730, a third fork 740, and a fourth fork 750 may be formed integral (i.e., monolithic) to one another and may be substantially rigid and non-movable relative to each other. First fork 720 may be held in an in-use position (FIG. 21) and/or a non-use position (FIG. 20) via a friction fit between outer surface 724 of fork 720 and an inner surface 713 of core 710. Alternatively, first fork 720 may be held in place relative to core 710 utilizing a set screw, shim, ratcheting, spring, or any means for maintaining the fork as depicted in FIG. 21, e.g., parallel to the other forks and bounding opening 725. Further, first fork 720 may be connected to core 710 via a pin or any other means for allowing the movability thereof relative to core 710.

Figure 21A:
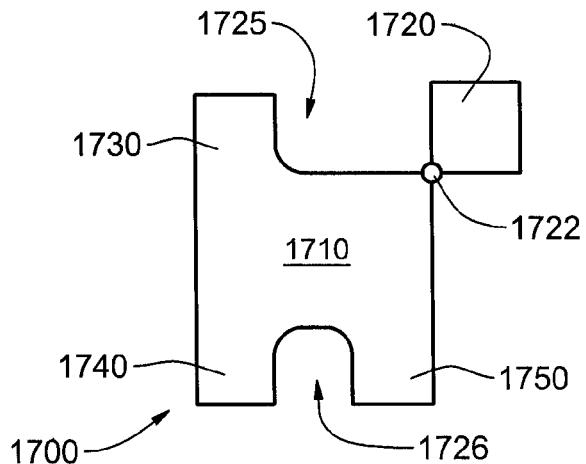
FIG. 21A is a front elevational view of a spinal implant in a non-use position, in accordance with an aspect of the present invention.

In another example depicted in FIG. 21A, an implant 1700 may include a fork 1720 hingedly or otherwise rotatably connected to a core 1710 about a hinge 1722. Core 1710 may include an upper fork 1730 and a lower fork 1740 along with a right lower fork 1750. Upper fork 1730 and fork 1720 may bound an opening 1725 for receiving an upper spinous process, such as upper spinous process 120 (FIG. 2). Lower fork 1740 and right lower fork 1750 may bound a cavity 1726 for receiving a lower spinous process, such as lower spinous process 130 (FIG. 2). As depicted in FIG. 21A, fork 1720 is in a non-use position while the rotation of fork 1720 in a counter-clockwise direction such that fork 1720 is substantially parallel to fork 1730 results in fork 1720 being located in an in-use position. As described for the other implants, fork 1720 may be held in the in-use positions via a set screw, ratcheting mechanism, shim, spring, or any other means of holding fork 1720 relative to core 1710.

Figure 22:
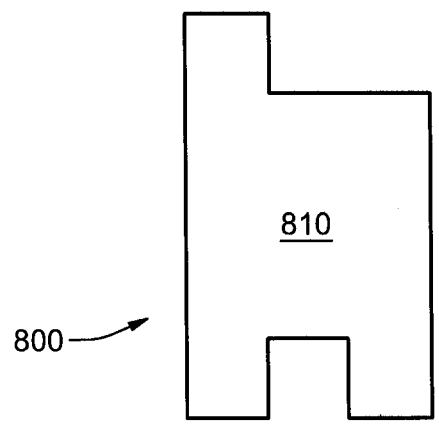
FIG. 22 is a front elevational view of a spinal implant, in accordance with an aspect of the present invention.
Figure 23:
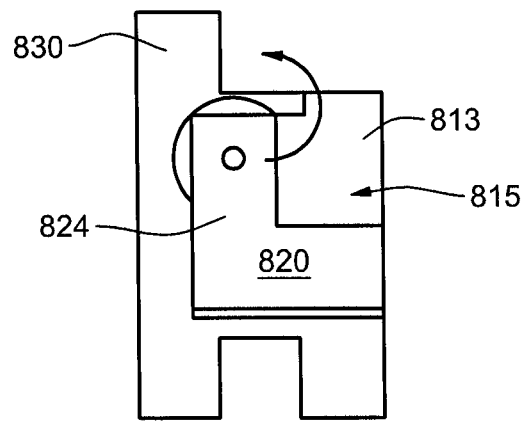
FIG. 23 is a front cross-sectional view of the implant of FIG. 22, in accordance with an aspect of the present invention.
Figure 24:
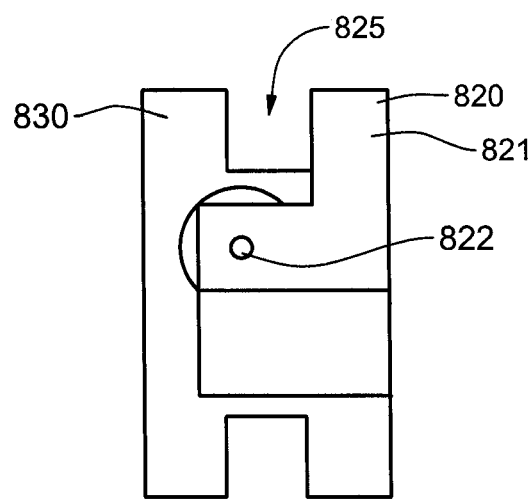
FIG. 24 is a front cross-sectional view of the implant of FIG. 22 in an in-use position, in accordance with an aspect of the present invention.

As depicted in FIGS. 22-24 in another example, an implant 800 may include a first fork 820 which is rotatable relative to a core 810. First fork 820 may have an L-shape and may be entirely received in a cavity 815 of core 810 when in a non-use position (FIGS. 22-23). The position of first fork 820 entirely within the cavity may allow the implant to be manipulated under or around the supraspinous ligament to avoid the necessity of cutting such ligament during the insertion thereof into an interspinous cavity, such as interspinous cavity 114. To arrive at an in-use position from the non-use position, fork 820 may be rotated about a pin 822 such that an extending portion 821 of fork 820 extending outside cavity 815 is substantially parallel to a second fork 830 and the forks bound an opening 825 configured (e.g., shaped and dimensioned) to receive an upper spinous process such as upper spinous process 120 (FIG. 2). Core 810 may be received in an interspinous space such as interspinous space 114 (FIG. 2). First fork 820 may be held in place relative to core 810 via a friction fit between outer surface 824 of fork 820 and an inner surface 813 of core 810. Alternatively, first fork 820 may be held in place relative to core 810 utilizing a set screw, ratcheting mechanism, shim, spring, or any other means of holding first fork 820 relative to core 810.

Figure 25:
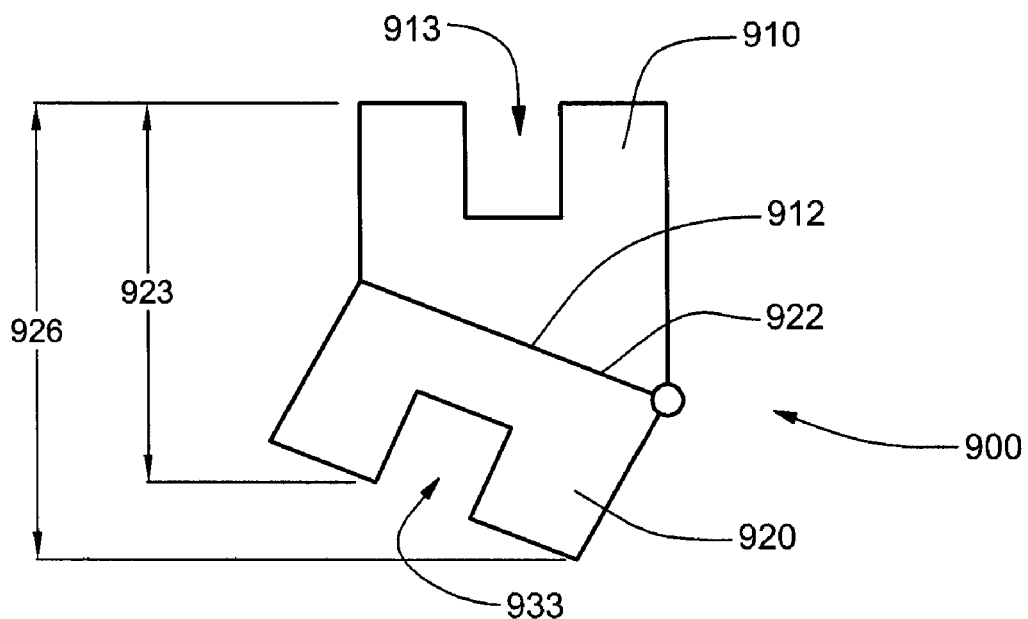
FIG. 25 is a front elevational view of a spinal implant in a non-use position, in accordance with an aspect of the present invention.
Figure 26:
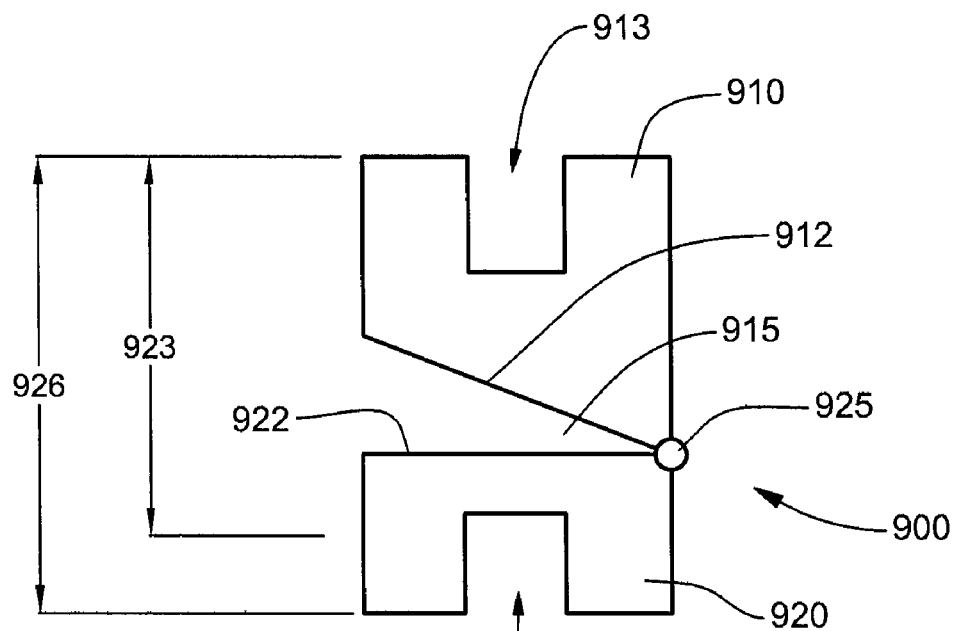
FIG. 26 is a front elevational view of the implant of FIG. 25 in an in-use position, in accordance with an aspect of the present invention.

In a further example depicted in FIGS. 25-26, an implant 900 includes a top member 910 pivotally connected to a bottom member 920 at a hinge, pivot or pin 925. In a non-use position depicted in FIG. 25, a bottom side 912 of top member 910 may abut a topside 922 of bottom member 920. In an in-use position depicted in FIG. 26, a cavity 915 may be present between bottom side 912 of top member 910 and topside 922 of bottom member 920. The compact nature of the non-use position depicted in FIG. 25 may allow the implant to be manipulated under or around the supraspinous ligament to avoid the necessity of cutting such ligament during the insertion thereof into a interspinous cavity, such as interspinous cavity 114. Such insertion may be facilitated by the difference in height between a minimum height 926 and a maximum height 924 of implant 900. In the non-use position a minimal left side height 923, which may be less than minimum height 926 as depicted, may further facilitate the insertion desired. To arrive at the in-use position from the non-use position, fork top member 910 and bottom member 920 may be rotated about pin 925 relative to each other from such minimum height to the maximum height.

Top member 910 and bottom member 920 may be held relative to one another in the in-use position as depicted in FIG. 26 by a shim, set screw, ratcheting mechanism, spring, or any other means of holding the members relative to one another such that they may maintain an upper spinous process (e.g. upper spinous process 120 (FIG. 3)) and a lower spinous process (e.g., lower spinous process 130 (FIG. 3)) at a desired position relative to one another. As depicted, top member 910 may include a cavity 913 for receiving a spinous process, such as upper spinous process 120 (FIG. 3), and bottom member 930 may include a cavity 933 for receiving an opposite spinous process, such as lower spinous process 130 (FIG. 3).

Figure 27:
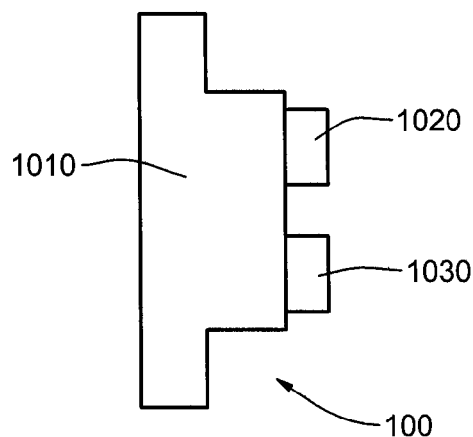
FIG. 27 is a front elevational view of an implant in a non-use position, in accordance with an aspect of the present invention.
Figure 28:
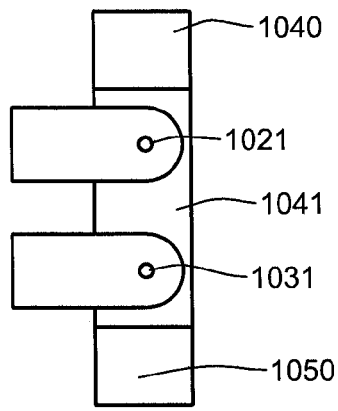
FIG. 28 is a side elevational view of the implant of FIG. 27, in accordance with an aspect of the present invention.
Figure 29:
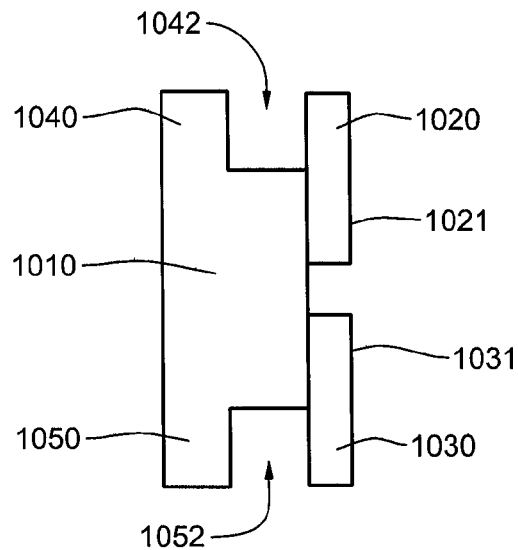
FIG. 29 is a front elevational view of the implant of FIG. 27 in an in-use position, in accordance with an aspect of the present invention.

In yet another example depicted in FIGS. 27-29, an implant 1000 includes a left side or core 1010 having a top right extending fork 1020 and a bottom right extending fork 1030 rotatably connected to core 1010 at first pin 1021 and second pin 1031, respectively. As depicted in FIGS. 27-28, forks 1020 and 1030 may be aligned about perpendicular to a top left fork 1040 and a bottom left fork 1050 in a non-use position. Top right extending fork 1020 and bottom right extending fork 1030 may be rotated about the respective pins to arrive at an in-use position depicted in FIG. 29. The axes of rotation may be aligned about parallel to the horizontal central portion of the H-shape of implant 1000 as depicted in FIG. 29. Top right extending fork 1020 and bottom right extending fork 1030 may be separated vertically by a space 1041 and may be rounded, as depicted in FIG. 27 to allow movement of the extending forks past one another during rotation to arrive at the in-use position depicted in FIG. 29. When in such in-use position, top right extending fork 1020 and top left extending fork 1040 may bound a cavity 1042 for receiving a top spinous process, such as top spinous process 120 (FIG. 3). Also, bottom right extending fork 1030 and bottom left extending fork 1050 may bound a cavity 1052 for receiving a bottom spinous process such as bottom spinous process 130 (FIG. 3). Core 1010 may provide support to such opposite spinous processes and the forks may extend vertically alongside such processes. Top right extending fork 1020 and bottom right extending fork 1030 may be held relative to one another in the in-use position as depicted in FIG. 29 by a shim, set screw, ratcheting mechanism, spring, or any other means of holding the forks relative to one another such that they bound the cavities for receiving the spinous processes.

Figure 29A:
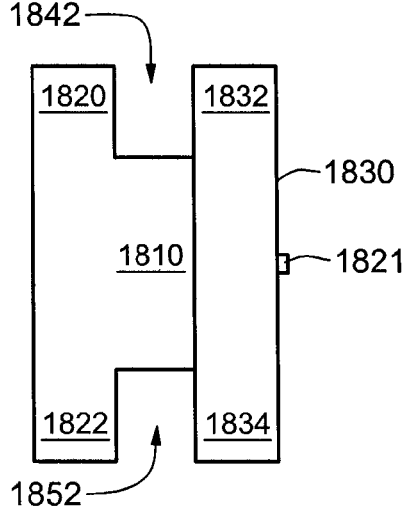
FIG. 29A is a front elevational view of the implant of FIG. 27 in an in-use position, in accordance with an aspect of the present invention.
Figure 29B:
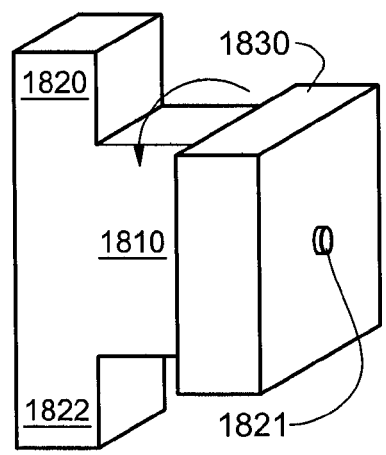
FIG. 29B is a front perspective view of the spinal implant of FIG. 29A in a non-use position, in accordance with an aspect of the present invention.

In another example depicted in FIGS. 29A-29B, an implant 1800 includes a core 1810 rotatably connected to a right side 1830 about a pin 1821. Right side 1830 may include an upper fork 1832 and a lower fork 1834. Core 1810 may include an upper left fork 1820 and a lower left fork 1822. Upper left fork 1820 and upper fork 1832 may bound an opening 1842 for receiving an upper spinous process (e.g., upper spinous process 120). Lower left fork 1820 and lower fork 1834 may bound an opening 1852 for receiving a lower spinous process (e.g., lower spinous process 130). FIG. 29B depicts implant 1800 in a non-use position and right side 1830 may be rotated to the in-use position depicted in FIG. 29A after insertion of implant 1800 into a desired interspinous space, such as interspinous space 114 (FIG. 2). As noted relative to the other implants, right side 1830 may be found in an in-use position and/or a non-use position via a set screw, shim, ratcheting mechanism, spring or any other means of holding the fork relative to the core such that the upper and lower forks bound the cavity for receiving spinous processes.

Figure 30:
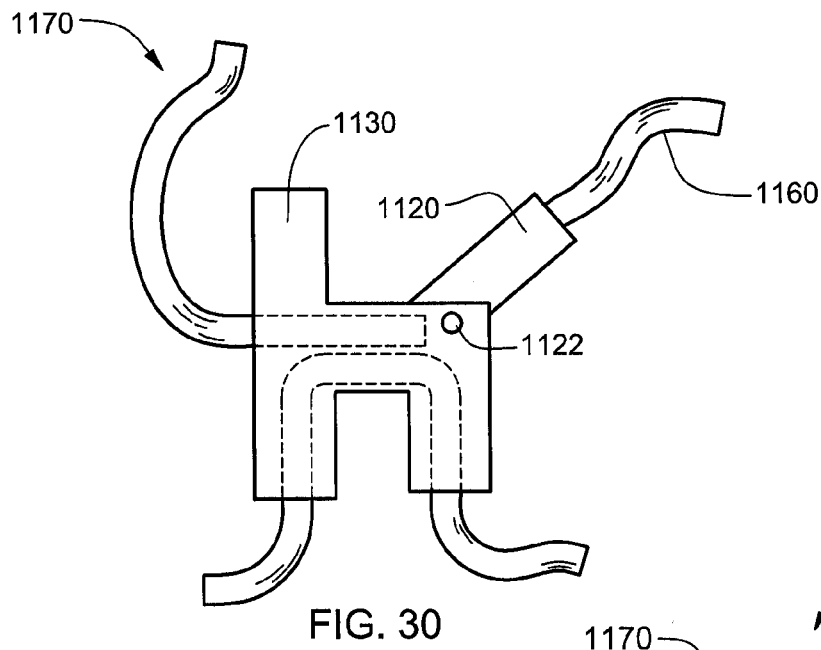
FIG. 30 is a front elevational view of a spinal implant in a non-use position, in accordance with an aspect of the present invention.
Figure 31:
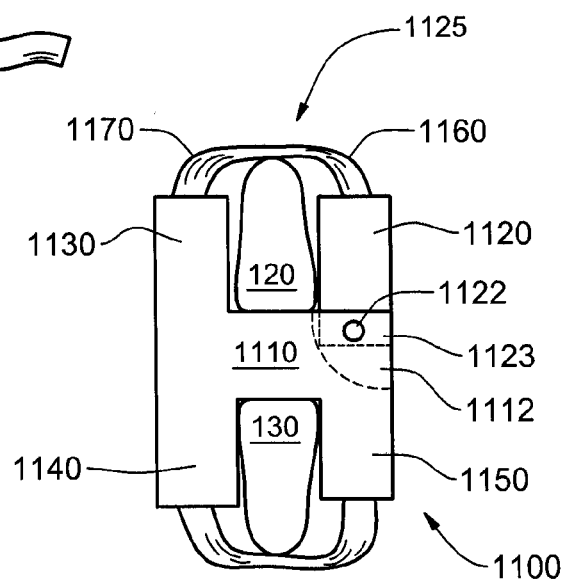
FIG. 31 is a front elevational view of the implant of FIG. 30 in an in-use position, in accordance with an aspect of the present invention.

In another example, FIGS. 30-31 depict an implant 1100 similar to implant 700 with the additional feature of a tether attached thereto. H-shaped implant 1100 may include a fork 1120 rotatably attached to a core 1110. Fork 1120 may be movable (e.g., rotatable about a pin 1122) from a first position as depicted in FIG. 30 to a second position depicted in FIG. 31. An internal end 1123 of fork 1120 may be received in a cavity 1112 of core 1110 and cavity 1112 may be formed in an arc shape to allow such rotation as depicted in phantom in FIG. 31. Fork 1120 may have a rectilinear cross-section, for example, as depicted in the figures.

Fork 1120 may be located in a non-use position in the first position (FIG. 30) which may facilitate the insertion of the implant into an interspinous space such as interspinous space 114 (FIG. 2). For example, the offset position of fork 1120 in FIG. 30 may allow the implant to be manipulated under or around the supraspinous ligament to avoid the necessity of cutting such ligament. When in the in-use position depicted in FIG. 31, fork 1120 and a second fork 1130 may be substantially parallel to each other and may bound an opening 1125 for receiving an upper spinous process such as upper spinous process 120. Core 1110, a second fork 1130, a third fork 1140, and a fourth fork 1150 may be formed integral (i.e., monolithic) to one another and may be substantially rigid and non-movable relative to each other. First fork 1120 has a first tether 1160 attached thereto and second fork 1130 has a second tether 1170 attached thereto. First fork 1120 may be held in an in-use position via the attaching of first tether 1160 to second tether 1170 around upper spinous process 120. Further, first fork 1120 may be connected to core 1110 via pin 1122 described above, or any other means for allowing movability thereof relative to core 1110. The attaching of the tethers to one another as depicted in FIG. 31 such that the processes are held in place relative to the implant and vice versa, allows the flexion of the spinous processes relative to one another as the tethers hold the processes relative to the implant. For example, the use of the tethers may allow a patient having an implant inserted between processes of the spine to have further support while leaning forward and may also maintain an upper and lower spinous process at a desired distance relative to one another.

Further, the tethers (e.g., tethers 1160, 1170) depicted may be attached to the implant or they may be formed integral thereto. For example, the tethers may be received in cavities or slots within the implants and ends of the tethers may be attached to one another to support the implants relative to the spinous processes and/or maintain the implants in a desired position relative to the processes. The tethers could be integral (e.g., monolithic) relative to the implant. For example, the tethers may be overmolded in the mold of the implant when the implant itself is formed.

Figure 32:
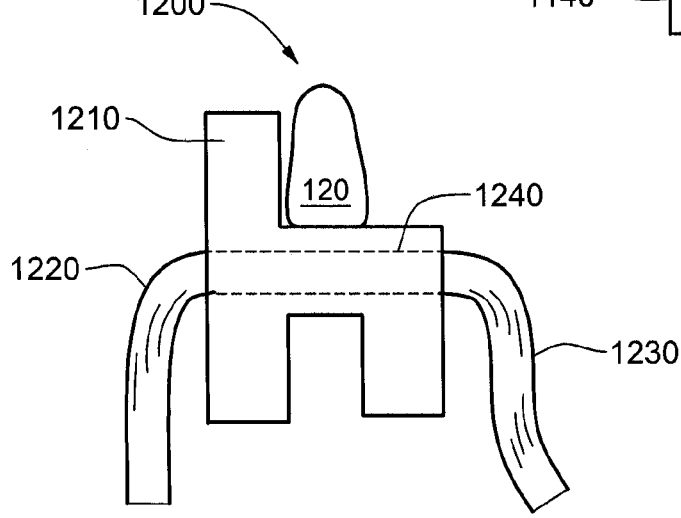
FIG. 32 is a front elevational view of a spinal implant in a non-use position, in accordance with an aspect of the present invention.

As depicted in FIG. 32, an implant 1200 may include a first fork 1210 along with a first tether 1220 and a second tether 1230. The implant may be inserted into an interspinous space and the tethers may be attached to each other around upper spinous process 120 similar to tethers 1160 and 1170 in FIGS. 30-31 without the use of a second fork opposite first fork 1210. First tether 1220 and second tether 1230 may be received in a cavity 1240 of implant 1200 or may be otherwise attached thereto. Implant 1200 may be inserted under or around the supraspinous ligament to avoid damaging the ligament, as described above for the other implants. The tethers may then be attached to one another to inhibit movement of the implant.

Figure 32A:
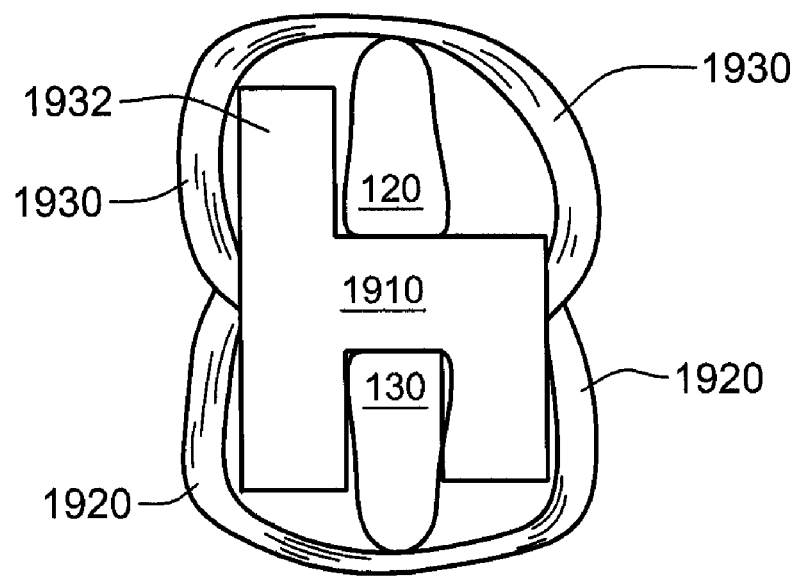
FIG. 32A is a front elevational view of a spinal implant in an in-use position, in accordance with an aspect of the present invention.

In another example depicted in FIG. 32A, an implant 1900 may include a core 1910 having a first tether 1920 and a second tether 1930. The tethers may be attached on opposite sides of the core 1910. Each of the tethers may wrap around opposite sides of the core and appropriate spinous processes to connect with one another. For example, core 1930 may be attached to a left side of core 1910 and may go along side a top left fork 1932 and may abut upper spinous process 1920 and may connect to tether 1920 at or near where tether 1920 is attached to core 1910. Similarly, tether 1920 may travel downwardly around lower spinous process 130 and the lower extending forks of core 1910 to connect to a left side of core 1910 at or near a point where tether 1930 is attached to core 1910. The tethers may be attached to core 1910 in any number of ways such as being formed integral (e.g., monolithic) thereto, being received in slots or cavities (not shown) thereof or via screws. Further, the tethers may be attached to each other by being tied to one another, for example.

Figure 32B:
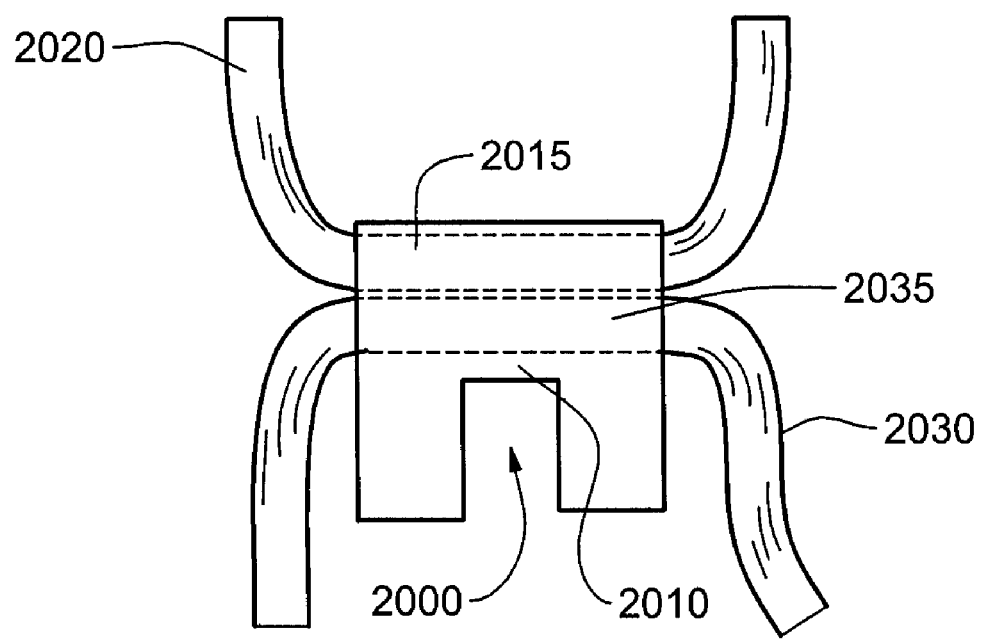
FIG. 32B is a front elevational view of a spinal implant in a non-use position, in accordance with an aspect of the present invention.

In another example depicted in FIG. 32B, an implant 2000 may include a core 2010 and may have a first tether 2020 received in a cavity 2015 thereof. Also, a second tether 2030 may be received in a second cavity 2035. In another example, the tethers could be received in the same cavity or the tethers could be formed integral (e.g., overmolded with) relative to core 2010. Similar to the depiction in FIG. 32A, opposite ends of the tethers may be attached to each other to secure them to the appropriate spinous process when core 2010 is received in an interspinous space, such as interspinous space 114.

Figure 33:
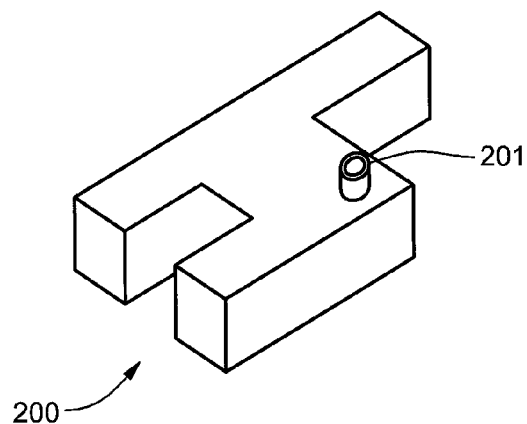
FIG. 33 is a perspective view of a spinal implant, in accordance with an aspect of the present invention.
Figure 34:
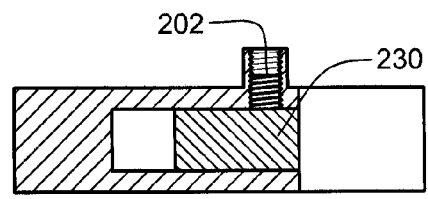
FIG. 34 is a side cross-sectional view of the implant of FIG. 33 in a non-use position, in accordance with an aspect of the present invention.
Figure 35:
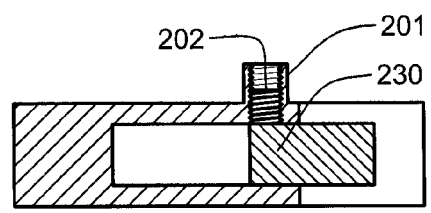
FIG. 35 is a side cross-sectional view of the implant of FIG. 33 in an in-use position, in accordance with an aspect of the present invention.
Figure 36:
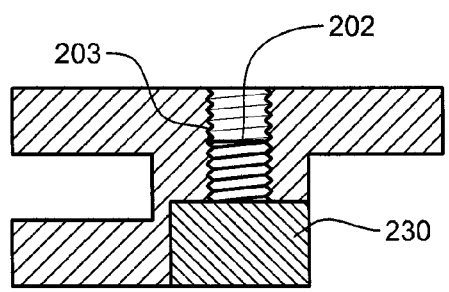
FIG. 36 is a top cross-sectional view of a spinal implant in a non-use position, in accordance with an aspect of the present invention.
Figure 37:
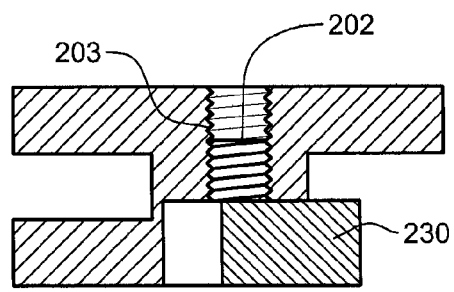
FIG. 37 is a top cross-sectional view of the implant of FIG. 36 in an in-use position, in accordance with an aspect of the present invention.

As described above, there are various means for maintaining forks positioned relative to cores, top and bottom members relative to each other, or other portions of spinal implants relative to a remainder of such implants including a friction fit, tether, set screw, ratcheting mechanism, spring, and shim. For example, as depicted in FIGS. 33-34, implant 200 may include a threaded boss 201 aligned in a width direction of the implant for receiving a set screw 202 to hold second fork 230 in position. FIG. 34 depicts a side cross-sectional view of a non-use position also depicted in FIG. 5, and FIG. 35 depicts a side view of an in-use position as also depicted in FIG. 4. Set screw 202 may be threaded into boss 201 to maintain second fork 230 in such non-use or in-use position. In an alternate embodiment depicted in FIGS. 36-37 a bore 203 configured (e.g., shaped and dimensioned) to receive the set screw may be aligned in a direction transverse to a height of implant 200 and in a lengthwise direction relative to the implant. Such a set screw may hold second fork 230 in a non-use in FIG. 36 and an in-use position in FIG. 37.

Figure 38:
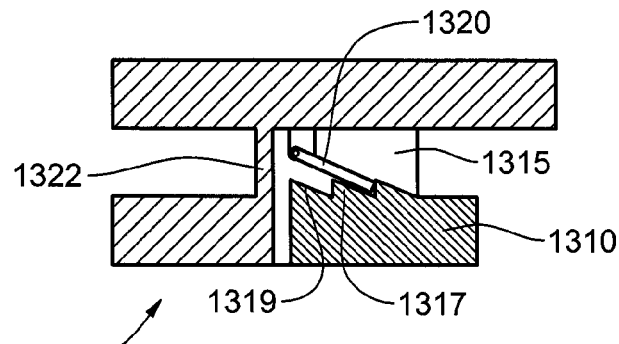
FIG. 38 is a top cross-sectional view of a spinal implant in a non-use position, in accordance with an aspect of the present invention.
Figure 39:
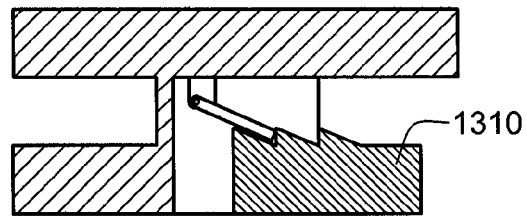
FIG. 39 is a top cross-sectional view of the implant of FIG. 38 in an in-use position, in accordance with an aspect of the present invention.
Figure 40:
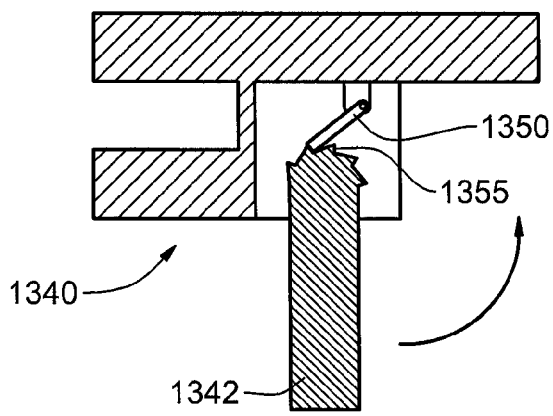
FIG. 40 is a top cross-sectional view of an implant in a non-use position, in accordance with an aspect of the present invention.
Figure 41:
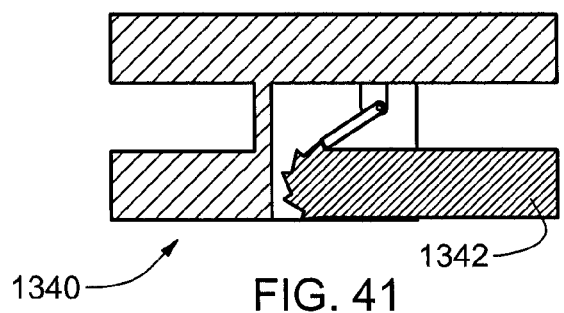
FIG. 41 is a top cross-sectional view of the implant of FIG. 40 in an in-use position.

FIGS. 38-39 depict an H-shaped implant 1300 similar to implant 200 (FIGS. 4-6) having a fork 1310 which is receivable in a cavity 1315. A ratchet mechanism 1320 is received in the cavity and is engageable with teeth 1317 on a side 1319 of fork 1310 such that ratchet 1320 engages with teeth 1317 to maintain fork 1310 in a particular position by inhibiting backward movement toward a core 1322 of implant 1300. FIG. 38 depicts a non-use position and FIG. 39 depicts an in-use position. FIGS. 40-41 depict a ratchet utilized with an implant 1340 which is similar to implant 700 depicted in FIGS. 19-21. A ratchet 1350 engages teeth 1355 of a fork 1342. As fork 1342 is rotated from a non-use position depicted in FIG. 40 to an in-use position depicted in FIG. 41, ratchet 1350 moves along teeth 1355 and retains fork 1342 in a particular position (i.e. by inhibiting backward rotation) according to the rotation of fork 1342 from the non-use position to the in-use position.

Figure 42:
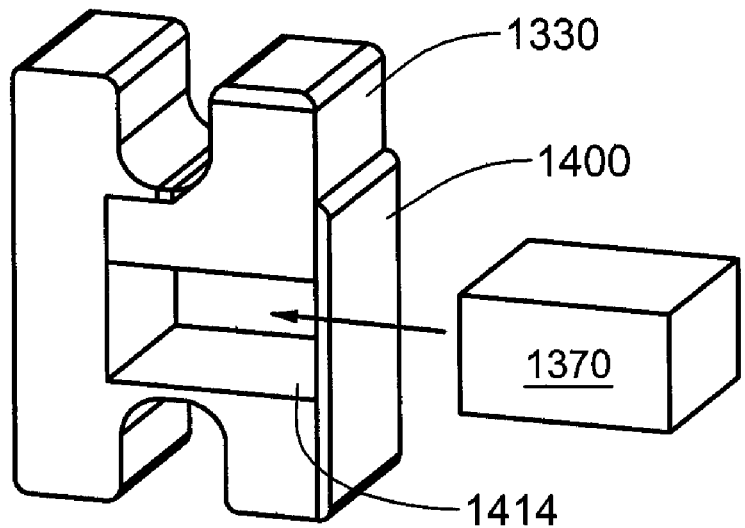
FIG. 42 is a perspective view of a spinal implant, in accordance with an aspect of the present invention.
Figure 43:
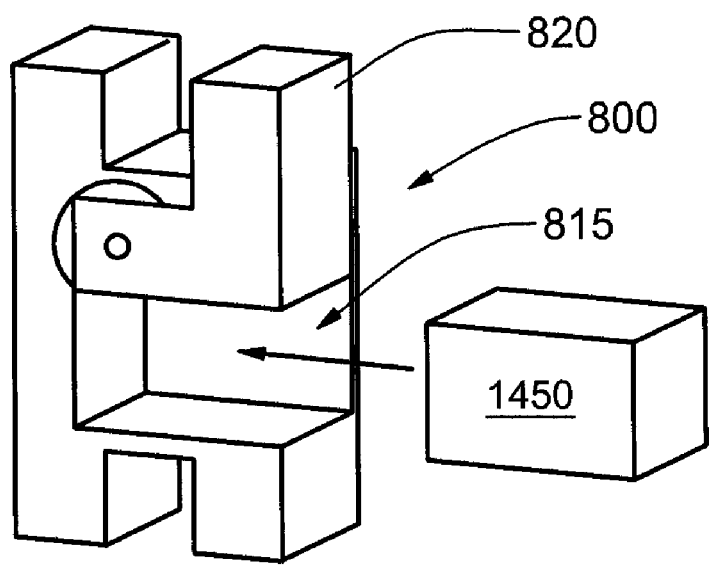
FIG. 43 is a perspective view of a spinal implant, in accordance with an aspect of the present invention.
Figure 44:
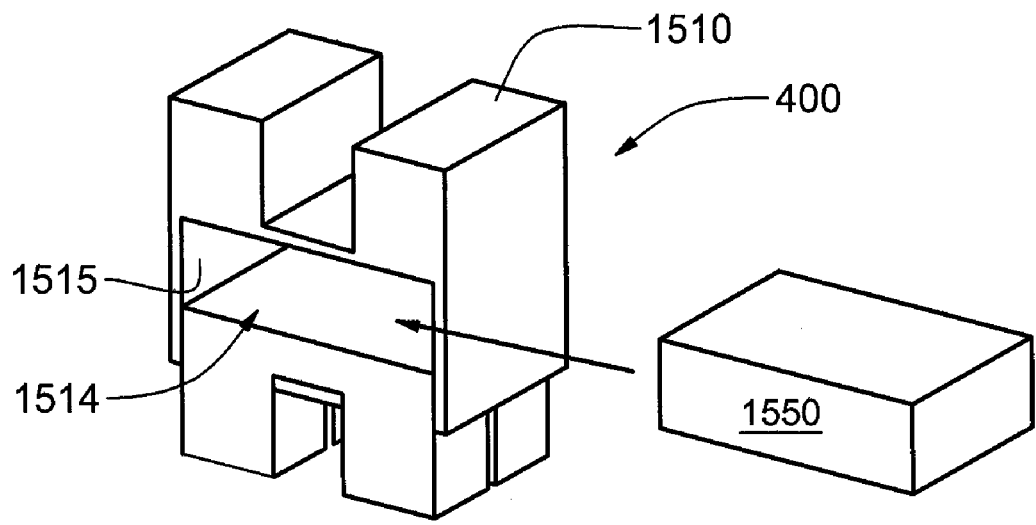
FIG. 44 is a perspective view of a spinal implant, in accordance with an aspect of the present invention.
Figure 45:
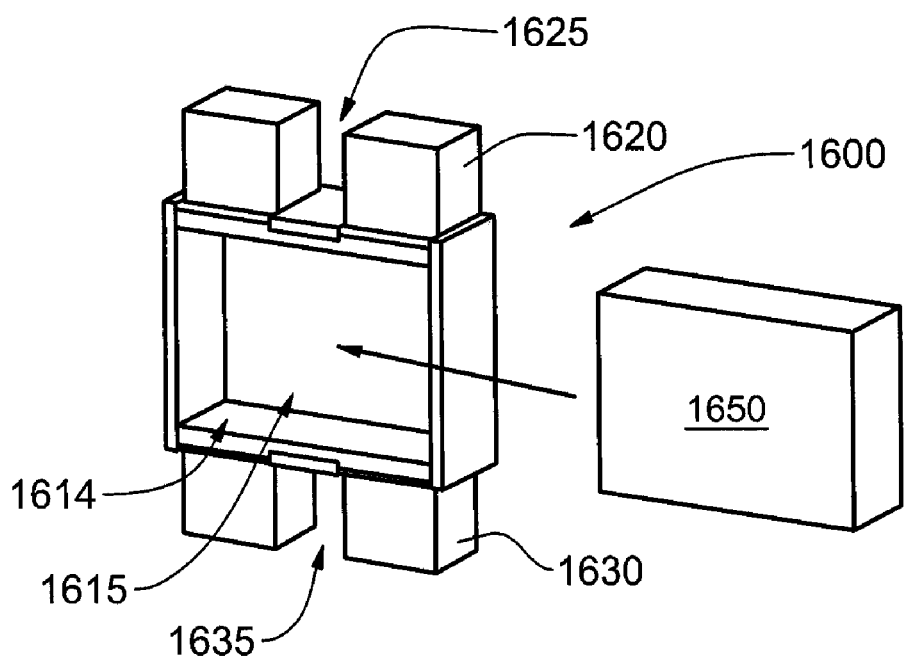
FIG. 45 is a perspective view of a spinal implant, in accordance with an aspect of the present invention.

FIGS. 42-45 depict the use of a shim with the embodiments similar or identical to those depicted in FIGS. 4-6, 10-16, and 22-24. For example, a shim 1370 may be received in an implant 1400 similar to implant 200 (FIGS. 4-6) except for an opening 1414 on a front side thereof to allow insertion of shim 1370 to maintain fork 1330, which is similar to fork 230, in an in-use position as depicted in FIG. 42. As depicted in FIG. 43, implant 800, also depicted in FIGS. 21-23, may receive a shim 1450 in cavity 815 in the in-use position to maintain fork 820 elevated such that fork 820 bounds cavity 825 configured to receive an upper spinous process, such as upper spinous process 120. Also, FIG. 44 depicts implant 1500, which is similar to implant 400 depicted in FIGS. 10-12 except for an opening 1514 in a front side thereof to allow shim 1550 to be received in a cavity 1515. Shim 1550 may hold upper member 1510 in an in-use position as depicted in FIG. 44 similar to implant 400 depicted in FIG. 10. FIG. 45 depicts implant 1600 receiving a shim 1650 through an opening 1614 in a cavity 1615. Implant 1600 is similar to implant 500 except for opening 1614 in a front side of implant 1600 to allow the shim to be inserted therein. As depicted in FIG. 45, shim 1650 may maintain top member 1620 and bottom member 1630 separated from one another such that an upper spinous process may be received in cavity 1625 and a lower spinous process may be received in cavity 1635 of top member 1620 and bottom member 1630. Also, although the embodiments depicted include openings for receiving shims, which are located in particular positions, the openings could be located in various positions on the implant, such as a top, bottom or the side(s) thereof.

Also, the forks and top and bottom members described above, which are movable between in-use and non-positions may be maintained in such in-use and/or non-use positions utilizing a spring or other biasing mechanism which may bias the implant in the in-use or non-use position. For example, the shims depicted in FIGS. 43-45 could be replaced by a spring which biases the forks toward an in-use position configured to bound upper and lower spinous processes. When utilizing a biasing mechanism such as a spring, a set screw or other means may be utilized to hold the implant in the non-use position prior to its insertion into the interspinous space.

It will be understood to one skilled in the art that the implants described could be formed of various materials which are biocompatible and which may maintain the spinous processes relative to one another in desired positions. For example, the described implants and portions thereof may be formed of rigid materials (e.g., metal, such as titanium, or stiff polymers), semi rigid materials (e.g. PEEK, a less stiff plastic or silicone), or a substantially flexible material (e.g., silicone or flexible plastic). For example, the implant described herein could have a modulus of elasticity substantially equal to a modulus of elasticity of bone, particularly the bone forming the spinous processes which the implants support. Also, it will be understood to one skilled in the art that the implants described herein could be formed of any shape (e.g., H-shaped, h-shaped, and n-shaped) such that the implants may be received between upper and lower spinous processes to support the spinous process and/or provide flexion or restraint to such spinous processes.

It will also be understood by one of ordinary skill in the art that the various means described of connecting and maintaining the forks, sections, members, and portions of the spinal implants positioned relative to each other could be utilized with each of the described implant embodiments. For example, the tethers described relative to implant 1200 could be utilized in conjunction with the other described embodiments to couple or connect the implants relative to the spinous processes. Also, any other means of connecting, supporting and positioning portions of the implants relative to other portions thereof could be utilized which allow the implant to be inserted into an interspinous space using a side-loading approach which avoids cutting the super spinous ligament. The implants could be loaded and manipulated from a non-use position to an in-use position from one side of the interspinous space (e.g., from a side of a mid-line of a spine of a patient). Alternatively, a portion of an implant could be inserted from one side of a mid-line of the spine (e.g., one side of the interspinous space) while a second portion of the implant could be inserted from the other side thereof.

Further, it will be understood by one of ordinary skill in the art that the forks, cores, top portions, bottom portions and other portions of the spinal implants described herein could be formed in any shape which facilitates their insertion into an interspinous space between spinous processes and allows the implant to support and/or separate the processes as desired.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. An interspinous spacer system comprising:
   a core having a shape configured to fit in an interspinous space between adjacent first and second spinous processes;
   a first fork being movable relative to said core from a non-use position to an in-use position; wherein when in said in-use position, the first fork extends outwardly from a first side of the core and has a first inner side bounding a first opening configured to receive the first spinous process;
   a second fork extending outwardly from a second side of said core opposite from the first side, said second fork having a second inner side bounding the first opening for receiving the first spinous process;
   third and fourth forks extending outwardly from the first and second sides of the core respectively and forming a second opening that faces away from the first opening and is configured to receive the second spinous process;

the second, third, and fourth forks affixed relative to the core and relative to each other;

wherein said first fork avoids protruding from said core to allow said core to be inserted into the interspinous space in said non-use position to avoid damage to a supraspinous ligament adjacent the space;

wherein said first fork is pivotally connected to said core.

2. The system of claim 1 wherein said first opening comprises a substantially U-shape in said in-use position and comprises a substantially L-shape in said non-use position.

3. The system of claim 2 wherein said U-shape is bounded by said first fork, said second fork and said core.

4. The system of claim 2 wherein said L-shape is bounded by said second fork and said core.

5. The system of claim 1 wherein said core and first, second, third, and fourth forks are substantially nonflexible.

6. The system of claim 1 wherein said core comprises a modulus of elasticity substantially equal to a modulus of elasticity of bone.

7. The system of claim 1 wherein said first fork is at least partially received in a cavity of said core in said non-use position.

8. The system of claim 7 wherein said first fork is entirely received in a cavity of said core in said non-use position.

9. An interspinous spacer system comprising:
a first core configured to fit in an interspinous space between adjacent first and second spinous processes;
first and second forks extending from said first core and forming a first saddle configured to receive the first spinous process;
a second core configured to fit in the interspinous space and having third and fourth forks extending from the second core; the third and fourth forks forming a second saddle that faces away from the first saddle and is configured to receive the second spinous process;
wherein the first and second cores are pivotally connected to one another about a hinge and are movable between a retracted position and a deployed position;
wherein the first and second saddles have first and second theoretical axes respectively extending therethrough, the first and second theoretical axes being spaced apart from the first, second, third, and fourth forks and extending substantially parallel to one another;
wherein the hinge has a pivot axis that extends substantially parallel to the first and second theoretical axes.

10. The spacer of claim 9 wherein when in the retracted position, a first surface of the first core engages a second surface of the second core and wherein when in the deployed position, the first surface of the first core is spaced apart from the second surface of the second core.

11. The spacer of claim 9 wherein first and second saddles each have a width and wherein the width of the saddles is the same in the retracted position and in the deployed position.

12. The spacer of claim 9 wherein the first fork of the first core and the third fork of the second core are disposed relatively closer together in the retracted position and are disposed relatively farther apart in the deployed position.

13. A method for spacing adjacent first and second spinous processes, the method comprising:
providing an interspinous spacer having a non-use position and an in-use position;
the spacer comprising a core and a plurality of forks extending from the core and configured to extend along opposing vertical sides of the spinous processes, the plurality of forks comprising a first, second, third, and fourth fork;

the first fork being movable relative to the core and relative to the second, third, and fourth forks;
the second, third, and fourth forks being affixed relative to the core and relative to each other;
wherein when in said in-use position, the first fork extends outwardly from the core and has an inner side bounding an opening configured to receive the first spinous process;
inserting the core, when the interspinous spacer is in the non-use position, into a space between the spinous processes from a side of a mid-line of a patient's spine such that the first spinous process is received in the opening;
while the first spinous process is received in the opening, moving the first fork relative to the core from the non-use position to the in-use position such that the first fork bounds the opening;
wherein the moving the first fork comprises pivoting the first fork relative to the core.

14. The method of claim 13 wherein the moving the first fork comprises extending the first fork from a cavity in the spacer to a position adjacent the first spinous process.

15. The method of claim 13 wherein the moving the fork comprises aligning the first fork of the implant adjacent the first spinous processes and substantially parallel to the second fork.

16. A method for spacing adjacent first and second spinous processes, the method comprising:
providing an interspinous spacer having a non-use position and an in-use position;
the spacer comprising;
a first core having first and second forks extending from the first core and forming a first saddle configured to receive the first spinous process;
a second core having third and fourth forks extending from the second core and forming a second saddle configured to receive the second spinous process;
wherein when coupled together, the first and second cores are pivotable relative to each other between a retracted position and a deployed position;
inserting the first and second cores, when the spacer is in the retracted position, into a space between the spinous processes from a side of a mid-line of a spine of a patient;
pivoting the first core relative to the second core about a hinge from the retracted position to the deployed position;
wherein pivoting the first core relative to the second core about a hinge comprises pivoting the first core about a pivot axis extending generally transverse to the first, second, third, and fourth forks.

17. The method of claim 16 further comprising maintaining the spacer in the deployed position by inserting a wedge into the cavity between the first and second saddles.

18. An interspinous spacer system comprising:
a core having a cavity configured to receive a top member and a bottom member;
the top member having first and second legs affixed relative to each other and forming a first saddle for receiving a first spinous process;
the bottom member having third and fourth legs affixed relative to each other and forming a second saddle for receiving a second spinous process;
the top and bottom members movable with respect to each other between a retracted position and a deployed position;
wherein in the retracted position the first saddle is disposed at least partially in the cavity;

wherein in the retracted position the first and second saddles are relatively closer together and in the deployed position the first and second saddles are relatively farther apart.

19. A method for spacing adjacent first and second spinous processes, the method comprising:
 providing an interspinous spacer having a non-use position and an in-use position;
 the spacer comprising;
  a first core having first and second forks extending from the first core and forming a first saddle configured to receive the first spinous process;
  a second core having third and fourth forks extending from the second core and forming a second saddle configured to receive the second spinous process;
  wherein when coupled together, the first and second cores are pivotable relative to each other between a retracted position and a deployed position;
 inserting the first and second cores, when the spacer is in the retracted position, into a space between the spinous processes from a side of a mid-line of a spine of a patient;
 pivoting the first core relative to the second core about a hinge from the retracted position to the deployed position;
 maintaining a width of the first and second saddles while pivoting the first core relative to the second core from the retracted position to the deployed position.

20. A method for spacing adjacent first and second spinous processes, the method comprising:
 providing an interspinous spacer having a non-use position and an in-use position;
 the spacer comprising;
  a first core having first and second forks extending from the first core and forming a first saddle configured to receive the first spinous process;
  a second core having third and fourth forks extending from the second core and forming a second saddle configured to receive the second spinous process;
  wherein when coupled together, the first and second cores are pivotable relative to each other between a retracted position and a deployed position;
 inserting the first and second cores, when the spacer is in the retracted position, into a space between the spinous processes from a side of a mid-line of a spine of a patient;
 pivoting the first core relative to the second core about a hinge from the retracted position to the deployed position;
 wherein the pivoting step comprises moving the first core relative to the second core from a position wherein the first fork is disposed relatively closer to the third fork to a position wherein the first fork is disposed relatively farther away from the third fork.

* * * * *